US008551699B2

(12) United States Patent
Bussemakers et al.

(10) Patent No.: US 8,551,699 B2
(45) Date of Patent: *Oct. 8, 2013

(54) PCA3, PCA3 GENES, AND METHODS OF USE

(75) Inventors: Marion J. G. Bussemakers, Nijmegen (NL); William B. Isaacs, Glyndon, MD (US)

(73) Assignees: Stichting Katholieke Universiteit, more particularly The University of Medical Centre Nijmegen, Nijmegen (NL); The Johns Hopkins University, Baltimore, MD (US)

( * ) Notice: Subject to any disclaimer, the term of this patent is extended or adjusted under 35 U.S.C. 154(b) by 740 days.

This patent is subject to a terminal disclaimer.

(21) Appl. No.: 12/609,483

(22) Filed: Oct. 30, 2009

(65) Prior Publication Data
US 2010/0047809 A1  Feb. 25, 2010

Related U.S. Application Data

(60) Continuation of application No. 11/260,282, filed on Oct. 28, 2005, now Pat. No. 7,632,643, which is a division of application No. 09/402,713, filed as application No. PCT/CA98/00346 on Apr. 9, 1998, now Pat. No. 7,008,765.

(60) Provisional application No. 60/041,836, filed on Apr. 10, 1997.

(51) Int. Cl.
C12Q 1/68 (2006.01)

(52) U.S. Cl.
USPC .......... 435/6.1; 435/6.11; 435/6.12; 435/6.14

(58) Field of Classification Search
None
See application file for complete search history.

(56) References Cited

U.S. PATENT DOCUMENTS

| | | | |
|---|---|---|---|
| 4,581,333 A | 4/1986 | Kourilsky et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,851,331 A | 7/1989 | Vary |
| 4,965,188 A | 10/1990 | Mullis et al. |
| 5,002,867 A | 3/1991 | Macevicz |
| 5,068,176 A | 11/1991 | Vijg et al. |
| 5,082,670 A | 1/1992 | Gage et al. |
| 5,112,736 A | 5/1992 | Caldwell et al. |
| 5,118,801 A | 6/1992 | Lizardi |
| 5,149,625 A | 9/1992 | Church et al. |
| 5,174,986 A | 12/1992 | Berns et al. |
| 5,175,383 A | 12/1992 | Leder et al. |
| 5,183,949 A | 2/1993 | Kindt et al. |
| 5,202,231 A | 4/1993 | Drmanac et al. |
| 5,219,989 A | 6/1993 | Sonenberg et al. |
| 5,283,174 A | 2/1994 | Arnold, Jr. et al. |
| 5,312,728 A | 5/1994 | Lizardi et al. |
| 5,399,491 A | 3/1995 | Kacian et al. |
| 5,422,252 A | 6/1995 | Walker et al. |
| 5,466,590 A | 11/1995 | Sariaslani et al. |
| 5,503,980 A | 4/1996 | Cantor |
| 5,547,842 A | 8/1996 | Hogan et al. |
| 5,554,516 A | 9/1996 | Kacian et al. |
| 5,585,481 A | 12/1996 | Arnold, Jr. et al. |
| 5,593,974 A | 1/1997 | Rosenberg et al. |
| 5,639,604 A | 6/1997 | Arnold, Jr. et al. |
| 5,656,207 A | 8/1997 | Woodhead et al. |
| 5,658,737 A | 8/1997 | Nelson et al. |
| 5,674,682 A | 10/1997 | Croce et al. |
| 5,773,705 A | 6/1998 | Vierstra et al. |
| 5,837,832 A | 11/1998 | Chee et al. |
| 5,861,242 A | 1/1999 | Chee et al. |
| 5,925,517 A | 7/1999 | Tyagi et al. |
| 5,939,258 A | 8/1999 | Croce et al. |
| 6,037,130 A | 3/2000 | Tyagi et al. |
| 6,087,133 A | 7/2000 | Dattagupta et al. |
| 6,110,678 A | 8/2000 | Weisburg et al. |
| 6,261,562 B1 | 7/2001 | Xu et al. |
| 6,262,245 B1 | 7/2001 | Xu et al. |
| 6,280,952 B1 | 8/2001 | Weisburg et al. |
| 6,287,820 B1 | 9/2001 | Umansky et al. |
| 6,383,739 B1 | 5/2002 | Kurth et al. |
| 6,395,278 B1 | 5/2002 | Xu et al. |
| 6,465,611 B1 | 10/2002 | Xu et al. |

(Continued)

FOREIGN PATENT DOCUMENTS

| | | |
|---|---|---|
| EP | 0125023 | 11/1984 |
| EP | 0160228 | 11/1985 |

(Continued)

OTHER PUBLICATIONS

PCT/CA00/01154, Aug. 16, 2001, ISR.
PCT/CA00/01154, Aug. 27, 2002, IPER.
PCT/EP05/014021, Aug. 11, 2006, ISR and WO.
PCT/EP05/014021, Jul. 5, 2007, IPRP.
PCT/CA98/00346, Aug. 25, 1998, ISR.
PCT/CA04/000170, Aug. 5, 2004, ISR and WO.
PCT/CA04/000170, Aug. 12, 2004, IPRP.
PCT/EP04/007124, Mar. 31, 2005, ISR and WO.
PCT/EP04/007124, Jan. 12, 2006, IPRP.
Altschul, S.F., et al., "Gapped BLAST and PSI-BLAST: a new generation of protein database search programs," Nucl. Acids Res. 25:3389-3402, Oxford University Press (1997).

(Continued)

*Primary Examiner* — Peter J Reddig
(74) *Attorney, Agent, or Firm* — Klarquist Sparkman, LLP

(57) ABSTRACT

The present invention relates, in general, to a prostate-specific antigen, PCA3. In particular, the present invention relates to nucleic acid molecules coding for the PCA3 protein; purified PCA3 proteins and polypeptides; recombinant nucleic acid molecules; cells containing the recombinant nucleic acid molecules; antibodies having binding affinity specifically to PCA3 proteins and polypeptides; hybridomas containing the antibodies; nucleic acid probes for the detection of nucleic acids encoding PCA3 proteins; a method of detecting nucleic acids encoding PCA3 proteins or polypeptides in a sample; kits containing nucleic acid probes or antibodies; bioassays using the nucleic acid sequence, protein or antibodies of this invention to diagnose, assess, or prognose a mammal afflicted with prostate cancer; therapeutic uses; and methods of preventing prostate cancer in an animal.

32 Claims, 17 Drawing Sheets

(56) References Cited

U.S. PATENT DOCUMENTS

| | | | |
|---|---|---|---|
| 6,479,263 | B1 | 11/2002 | Slawin et al. |
| 6,528,260 | B1 | 3/2003 | Blumenfeld et al. |
| 6,534,273 | B2 | 3/2003 | Weisburg et al. |
| 6,551,778 | B1 | 4/2003 | Harvey et al. |
| 6,800,746 | B2 | 10/2004 | Xu et al. |
| 6,897,024 | B2 | 5/2005 | Bussemakers et al. |
| 7,008,765 | B1 | 3/2006 | Bussemakers et al. |
| 7,138,235 | B2 | 11/2006 | Bussemakers et al. |
| 7,368,545 | B1 | 5/2008 | Busse et al. |
| 7,632,643 | B2 | 12/2009 | Bussemakers et al. |
| 2002/0022248 | A1 | 2/2002 | Xu et al. |
| 2002/0035244 | A1 | 3/2002 | Cohen et al. |
| 2002/0168638 | A1 | 11/2002 | Schlegel et al. |
| 2003/0165850 | A1 | 9/2003 | Bussemakers et al. |
| 2005/0158792 | A1 | 7/2005 | Bussemakers et al. |
| 2005/0164223 | A1 | 7/2005 | Schalken et al. |
| 2005/0282170 | A1 | 12/2005 | Fradet et al. |
| 2006/0099658 | A1 | 5/2006 | Bussemakers et al. |
| 2010/0021884 | A1 | 1/2010 | Hessels et al. |

FOREIGN PATENT DOCUMENTS

| | | |
|---|---|---|
| EP | 0171496 | 2/1986 |
| EP | 0173494 | 5/1986 |
| EP | 0184187 | 11/1986 |
| EP | 0256932 | 2/1988 |
| EP | 0520794 | 12/1992 |
| EP | 0320308 | 3/1993 |
| EP | 0747706 | 12/1996 |
| EP | 1295125 | 5/2006 |
| WO | WO 86/01533 | 3/1986 |
| WO | WO 87/02671 | 10/1986 |
| WO | WO 90/00944 | 2/1990 |
| WO | WO 91/19008 | 12/1991 |
| WO | WO 93/03743 | 4/1993 |
| WO | WO 93/08845 | 5/1993 |
| WO | WO 93/13121 | 7/1993 |
| WO | WO 94/09820 | 5/1994 |
| WO | WO 94/15646 | 7/1994 |
| WO | WO 95/28498 | 10/1995 |
| WO | WO 95/32305 | 11/1995 |
| WO | WO 96/11266 | 4/1996 |
| WO | WO 96/14875 | 5/1996 |
| WO | WO 96/32966 | 10/1996 |
| WO | WO 98/02582 | 1/1998 |
| WO | WO 98/45420 | 10/1998 |
| WO | WO 00/04149 | 1/2000 |
| WO | WO 00/50899 | 8/2000 |
| WO | WO 00/58470 | 10/2000 |
| WO | WO 01/23550 | 4/2001 |
| WO | WO 01/25272 | 4/2001 |
| WO | WO 01/25273 | 4/2001 |
| WO | WO 01/34802 | 5/2001 |
| WO | WO 01/44507 | 6/2001 |
| WO | WO 01/51633 | 7/2001 |
| WO | WO 01/60860 | 8/2001 |
| WO | WO 01/73032 | 10/2001 |
| WO | WO 02/24718 | 3/2002 |
| WO | WO 02/30268 | 4/2002 |
| WO | WO 2004/070056 | 8/2004 |

OTHER PUBLICATIONS

Armbruster et al., "Enzyme immunoassay, kinetic microparticle immunoassay, radioimmunoassay, and fluorescence polarization immunoassay compared for drugs-of-abuse screening", Clin Chem. 39(10):2137-46 (1993).

Arnold, Jr., L.J., et al., "Assay Formats Involving Acridinium-Ester-Labe/ed DNA Probes," Clin. Chem. 35:1588-1594, American Association for Clinical Chemistry (1989).

Auffray C, Rougeon F. "Purification of mouse immunoglobulin heavy-chain messenger RNAs from total myeloma tumor RNA". Eur J Biochem 1980;107:303-14.

Barbu V, Dautry F. "Northern blot normalization with a 28S rRNA oligonucleotide probe". Nucleic Acids Res 1989;17:7115.

Beduschi MC, Oesterling JE. "Percent free prostate-specific antigen: the next frontier in prostate-specific antigen testing". Urology 51:98-109 (1998).

Bernard PS, Wittwer CT. "Real-time PCR technology for cancer diagnostics". Clin Chem. 48:1178-85 (2002).

Black, D.L., "Mechanisms of Alternative Pre-Messenger RNA Splicing," Annu. Rev. Biochem. 72:291-336 (Feb. 2003).

Boom, R., et al., "Rapid and Simple Method for Purification of Nucleic Acids," J. Clin, Microbiol. 28:495-503, American Society for Microbiology (1990).

Boulikas, T., "Gene Therapy of Prostate Cancer: p53, Suicidal Genes, and Other Targets," Anticancer Res. 17:1471-1505, International Institute of Anticancer Research (1997).

Bowie, J.U., "Deciphering the Message in Protein Sequences: Tolerance to Amino Acid Substitutions," Science 247:1306-1311, American Association for the Advancement of Science (1990).

Brakebusch, C., et al., "Expression of the 90K Immunostimulator Gene Is Controlled by a Promoter with Unique Features," J. Biol. Chem. 272:3674-3682, The American Society for Biochemistry and Molecular Biology, Inc. (1997).

Brawer et al., "Screening for prostatic carcinoma with prostate specific antigen". J Urol 147:841-5 (1992).

Brawer MK. "Prostate-specific antigen". Semin Surg Oncol. 18:3-9 (2000).

Chitale and Khubchandani, "Interpretation of Prostatic Biopsies: A Review", The Internet Journal of Urology. 3(1), (2005).

Brinster et al., "Factors affecting the efficiency of introducing foreign DNA into mice by microinjecting eggs", PNAS. 82 (13):4438-4442 (1985).

Brown, A.M., "A step-by-step guide to non-linear regression analysis of experimental data using a Microsoft Excel spreadsheet," Comput. Methods Programs Biomed. 65:191-200, Elsevier Scientific Publishers (Jun. 2001).

Buck, G.A., et al., "Design Strategies and Performance of Custom DNA Sequencing Primers," BioTechniques 27:528-536, Informa Healthcare USA, Inc. (Sep. 1999).

Burgess, W.H., et al., "Possible Dissociation of the Heparin-binding and Mitogenic Activities of Heparin-binding (Acidic Fibroblast) Growth Factor-1 from its Receptorbinding Activities by Site-directed Mutagenesis of a Single Lysine Residue," J Cell. Biol. / / / :2129-2138, The Rockefeller UMversity Press (1990).

Bussemakers et al., "DD3: a new prostate-specific gene, highly overexpressed in prostate cancer", Amer Assoc Cancer Research, 59:5975-9 (1999).

Bussemakers, M.J .G., et al., "DD3: a new prostate specific marker, overexpressed in prostatic tumors," Proc. Annu. Meet. Amer. Assoc. Cancer Res. 87:515, Abstract No. 3522, 87th Annual meeting of the American Association for Cancer Research (1996).

Bussemakers, M.J., and Isaacs, W.B., "Identification of Genes Associated with Prostate Cancer Development," Urol. Res. 21:452, Abstract No. P42, Springer International (1993).

Bussemakers, M.J.G., "Changes in Gene Expression and Targets for Therapy," Eur. Urol. 35:408-412, Elsevier Science (Jan. 1999).

Bussemakers, M.J.G., et al., "Assessment of the Clincial Usefulness of the Prostate-Cancer-Specific DD3 Gene," Eur. Urol. 36: 508, Abstract No. 0139, Elsevier Science (Nov. 1999).

Bussemakers, M.J.G., et al., "DD3: A New Prostate Specific Marker, Overexpressed in Prostatic Tumors," Presented at Breast and Prostate Cancer: Basic Mechanisms, Taos, New Mexico, Abstract No. 102, 1 page (Jan. 29-Feb. 4, 1996).

Bussemakers, M.J.G., et al., "DD3: A New Prostate Specific Marker, Overexpressed in Prostatic Tumors," Presented at Meeting for the Dutch Association for Tumor Cell Biology, May, The Netherlands, 1 page (1996).

Bussemakers, M.J.G., et al., "DD3: A New Prostate-Specific Marker, Strongly Overexpressed in Prostatic Tumors," Urol. Res. 25:76, Abstract No. 02.2, Springer International (1997).

Bussemakers, M.J.G., et al., "Identification of DD3: A New Gene Overexpressed in Prostatic Tumors," Urol. Res. 23:253, Abstract No. 0 36, Springer International (1995).

Bussemakers, MJ.G., and Isaacs, W.B., "Identification of Genes Associated with Prostate Cancer Development," Presented at 8th

(56) References Cited

OTHER PUBLICATIONS

Annual Spring Meeting, May 13-May 14, San Fransico, CA, one page, Society for Basic Urologic Research (1994).
Bussemakers, MJ.G., et al., "DD3: A New Prostate Specific Marker, Overexpressed in Prostatic Tumors," Presented at Fall Symposium, Dec. 7-10, Chapel Hill, North Carolina, 1 page, Society for Basic Urologic Research (1995).
Bustin SA. "Absolute quantification of mRNA using real-time reverse transcription polymerase chain reaction assays", J Mol Endocrinol 2000;25:169-93.
Cairns, P., et al., "Molecular Detection of Prostate Cancer in Urine by GSTP1 Hypermethylation," Clin. Cancer Res. 7:2727-2730, The American Association for Cancer Research (Sep. 2001).
Catalona et al., "Measurement of prostate-specific antigen in serum as a screening test for prostate cancer". N Engl J Med, 324:1156-61 (1991).
Cheung, R.C., et al., "Rapid and Sensitive Method for Detection of Hepatitis C Virus RNA by Using Silica Particles," J. Clin. Microbiol. 10:2593-2597, American Society for Microbiology (1994).
Clements, J.A., et al., "Molecular Detection of Prostate Cells in Ejaculate and Urethral Washings in Men With Suspected Prostate Cancer," J. Urol. 161:1337-1343, Lippincott Williams & Wilkins (Apr. 1999).
Cleutjens, K.B.J.M., et al., "A 6-kb Promoter Fragment Mimics in Transgenic Mice the Prostate-Specific and Androgen-Regulated Expression of the Endogenous Prostate-Specific Antigen Gene in Humans," Mol. Endocrinol. I 1:1256-1265, The Endocrine Society (1997).
Cleutjens, K.B.J.M., et al., "An Androgen Response Element in a Far Upstream Enhancer Region Is Essential for High, Androgen-Regulated Activity of the Prostate-Specific Antigen Promoter," Mol. Endocrinol. 11:148-161, The Endocrine Society (1997).
Database EMBL Online, Bussemakers et al., Accession No. AF103908 (Nov. 1999).
Database NCBI Entrez, GenBank Report, Accession No. AL359314 (May 2001).
Database NCBI, Accession No. AF103907 (Aug. 2000).
Database NCBI, Accession No. AF103908 (Aug. 2000).
de Kok et al., DD3(PCA3), a very sensitive and specific marker to detect prostate tumors. Amer Assoc Cancer Res. 62:2695-8 (2002).
Deras et al., "PCA3: A molecular urine assay for preicting prostate biopsy outcome", J Urol 179:1587-1592 (2008).
Dieffenbach et al., "General concepts for PCR primer design", PCR Methods Appl. 3:30-37 (1993).
Edery, I., et al., "High-level synthesis in *Escherichia coli* of functional cap-binding eukaryotic initiation factor eIF-4E and affinity purification using a simplified cap-analog resin," Gene 74:517-525, Elsevier/North-Holland (1988).
El-Shirbiny, A.M., "Prostatic Specific Antigen," Adv. Clinical Chem. 31:99-133, Academic Press, Inc. (1994).
Ferrari AC, Stone NN, Eyler JN, Gao M, Mandeli J, Unger P et al. Prospective analysis of prostate-specific markers in pelvic lymph nodes of patients with high risk prostate cancer. J Natl Cancer Inst 1997;89:1498-504.
Watala et al., "Multivariate relationships between international normalized ratio and vitamin K-dependent coagulation-derived parameters in normal healthy donors and oral anticoagulant therapy patients", Thrombosis Journal, 30;1(1):7 (2003).
Wei, C., et al., Tissue-specific expression of the human prostate-specific antigen gene in transgenic mice: Implications for tolerance and immunotherapy, Proc. Natl. Acad. Sci. USA 94:6369-6374, The National Academy of Sciences of the USA (1997).
Weiss, R., "Hot Prospect for New Gene Amplifier," Science 254:1292-1293, American Association for the Advancement of Science (1991).
Xu et al., "Expression profile of an androgen regulated prostate specific homeobox gene NKX3.1 in primary prostate cancer". J Urol. 163:972-9 (2000).

Yelin et al., "Widespread occurrence of antisense transcription in the human 1, genome," Nat. Biotechnol. 21 :379-386, Nature Publishing Group (Apr. 2003).
Ylikoski et al., "Dual-label detection of amplified products in quantitative RT-PCR assay using lanthanide-labeled probes". Biotechniques. 30:832-6, 838, 840 (2001).
Ylikoski et al., "Quantitative reverse transcription-PCR assay with an internal standard for the detection of prostate-specific antigen mRNA". Clin Chem. 45:1397-407 (1999).
Murphy et al., "Evaluation and comparison of two new prostate carcinoma markers. Freeprostate specific antigen and prostate specific membrane antigen". Cancer. 78:809-18 (1996).
Nelson et al., "Molecular cloning and characterization of prostate, an androgen-regulated serine protease with prostate-restricted expression". Proc Natl Acad Sci USA 96:3114-9 (1999).
Nielsen, P.E., "Applications of peptide nucleic acids," Curr. Opin. Biotechnol. 10:71-75, Elsevier Science Ltd. (Feb. 1999).
Nixon RG, Brawer MK. Enhancing the specificity of prostate-specific antigen (PSA): an overview of PSA density, velocity and age-specific reference ranges. Br J Urol 1997;79 Suppl 1:61-7.:61-7.
Nurmi et al., "High-performance real-time quantitative RT-PCR using lanthanide probes and a dual-temperature hybridization assay". Anal Chem 2002;74:3525-32.
Oettgen et al., "PDEF, a novel prostate epithelium-specific ets transcription factor, interacts with the androgen receptor and activates prostate-specific antigen gene expression". J Biol Chem 275:1216-25 (2000).
Office Action for U.S. Appl. No. 09/996,953, inventors Bussemakers, M.J., et al., filed Nov. 30, 2001, mailed on Aug. 26, 2003.
Pang, S., et al., "Identification of a Positive Regulatory Element Responsible for Tissue-specific Expression of Prostate-specific Antigen," Cancer Res. 57:495-499, The American Association for Cancer Research (1997).
Partin et al., "Complexed Prostate Specific Antigen Improves Specificity for Prostate Cancer Detection: Results of a Prospective Multicenter Clinical Trial", Journal of Urology, 170(5):1787-1791 (2003).
Paule MR, White RJ. Survey and summary: transcription by RNA polymerases I and I II. Nucleic Acids Res 2000;28:1283-98.
Polascik et al., "Prostate specific antigen: a decade of discovery—what we have learned and where we are going". J Urol. 62:293-306 (1999).
Quandt, K., et al., "MatInd and MatInspector: new, fast and versatile tools for detection of consensus matches in nucleotide sequence data," Nucl. Acids Res. 23:4878-4884, Oxford University Press (1995).
Raeymaekers L. "Quantitative PCR: theoretical considerations with practical implications". Anal Biochem. 214:582-5 (1993).
Rieger-Christ, K., et al., "Identification of Fibroblast Growth Factor Receptor 3 Mutations in Urine Sediment DNA Samples Complements Cytology in Bladder Tumor Detection," Cancer 98:737-744, American Cancer Society (Aug. 2003).
Ringsrud, K.M., "Cells in the Urine Sediment," Lab. Med. 32:153-155, American Society for Clinical Pathology (Mar. 2001).
Rubanyi, G.M., "The future of human gene therapy," Mol. Aspects Med. 22:113-142, Elsevier Science (Jun. 2001).
Rubin and Levy, "A mathematical model and a computerized simulation of PCR using complex templates", Nucleic Acids Research, 24(18):3538-3545 (1996).
Rychlik and Rhaods, "A computer program for choosing optimal oligonucleotides for filter hybridization, sequencing and in vitro amplification of DNA", Nucleic Acids Research, 17(21):8543-8551 (1989).
Rychlik, W, "Chapter 2: Selection of primers for polymerase chain reaction", from Methods in Molecular Biology vol. 15. PCR Protocols: Current methods and applications. Ed. Bruce A, White, Humana Press Inc, pp. 31-40 (1993).
Schalken et al., "New targets for therapy in prostate cancer: Differential display code 2 (DD3(PCA3)), a highly prostate cancer-specific gene", Urology 62(Suppl. 5A):34-43 (2003).
Schalken, J., "Molecular Diagnostics and Therapy of Prostate Cancer: New Avenues," Eur. Urol. 34 Suppl 3:3-6, S. Karger AG (1998).

(56) References Cited

OTHER PUBLICATIONS

Schuur, E.R., et al., "Prostate-specific Antigen Expression Is Regulated by an Upstream Enhancer," J. Biol. Chem. 271:7043-7051, The American Society for Biochemistry and Molecular Biology, Inc. (1996).
Schwartz, C.J., et al., "FTZ—FactorI and Fushi tarazu interact via conserved nuclear receptor and coactivator motifs," EMBO J 20:510-519, Oxford University Press (Feb. 2001).
Sequence Comparisions in Office Action for U.S. Appl. No. 10/773,440, inventors Fradet, Y. et al., filed Feb. 9, 2004, mailed on Jun. 23, 2006.
Sharrocks, AD, "Chapter 2: The design of primers for PCR", from PCT Technology Current Innovations. Eds. Hugh G, Griffin and Annette M. Griffin. CRC Press pp. 5-11 (1994).
Sidransky, D., "Nucleic acid-based methods for the detection of cancer", Science, 278(5340):1054-9 (1997).
Smith et al., "Prostate-specific antigen messenger RNA is expressed in non-prostate cells: implications for detection of micrometastases". Cancer Res. 55:2640-4 (1995).
Soini E, Lovgren T. "Time-resolved fluorescence of lanthanide probes and applications in biotechnology". CRC Crit Rev Anal Chem. 18:105-54 (1987).
Srikantan et al., "PCGEM1, a prostate-specific gene, is overexpressed in prostate cancer". Proc Natl Acad Sci USA Oct. 24, 2000;97(22):12216-21 2001;97:12216-21.
Strickler, H.D., and International SV40 Working Group, "A Multicenter Evaluation of Assays for Detection of SV40 DNA and Results in Masked Mesothelioma Specimens," Cancer Epidemiol. Biomarkers Prev. 10:523-532, American Association for Cancer Research (May 2001).
Sun Y, Lin J, Katz AE, Fisher PB. Human prostatic carcinoma oncogene PTI-1 is expressed in human tumor cell lines and prostate carcinoma patient blood samples. Cancer Res 1997;57:18-23.
Sutcliffe, J.G. et al., "Antibodies That React with Predetermined Sites on Proteins," Science 219:660-666, Association of the Advancement of Science (1983).
Syfpeithi at http://134.2.96.221/scripts/MHCServer,d11/home.htm (Mar. 13, 2001).
Tamimi, Y., et al., "DiagnoGene PCA3 reliable NASBA based reagents for detecting PCA3 niRNA, a recently described prostate marker," Proc. Am. Assoc. Cancer Res. 39:234 Poster Abstract, Williams & Wilkins (Mar. 1998).
Taneja, S.S., et al., "Chapter 23: Gene Therapy: Principles and Potential," in Cancer Surveys: Preventing Prostate Cancer: Screening versus Chemoprevention, Oliver, R.T.D., et al., eds., Cold Spring Harbor Laboratory Press, pp. 247-266 (1995).
Tinzl et al., "DD3OPCA3 RNA analysis in urine—a new perspective for detecting prostate cancer." European Urology. 46(2):182-186 (2004).
Tockman, M.S., et al., "Considerations in Bringing a Cancer Biomarker to Clinical Application," Cancer Res. 52:2711s-2718s, American Association for Cancer Research (1992).
Torres and Marks, "PCS3: A genetic marker of prostate cancer", PCRI Insights. New developments in prostate cancer treatment. 9(3):4-9 (2006).
Tyagi, S., and Kramer, F.R., "Molecular Beacons: Probes that Fluoresce upon Hybridi7ation," Nat. Biotechnol. 14:303-308, Nature Publishing Group (1996).
Ukimura et al., "Role of PSA and its indices in determining the need for repeat prostate biopsies". Urology 1997;50:66-72.
Vallejo et al., "In vitro synthesis of novel genes: mutagenesis and recombination by PCR", PCR Methods Appl. 4:123-130 (1994).
Vandesompele et al., "Accurate normalization of real-time quantitative RT-PCR data by geometric averaging of multiple internal control genes". Genome Biol 3: RESEARCH0034 (2002).
Verhaegh, G.W., et al., "Isolation and Characterization of the Promoter of the Human Prostate Cancer-specific DD3 Gene," J. Biol. Chem. 275:37496-37503, The American Society for Biochemistry and Molecular Biology (Dec. 2000).

Verkaik, N.S. et al., "Clinical usefulness of RT-PCR detection of hematogenous prostate cancer spread," Urol. Res. 25:373-384, Springer-Verlag (1997).
Verma, I.M., and Somia, N., "Gene therapy—promises, problems and prospects", Nature 389:239-242, Nature Publishing Group (1997).
Voet, D., and Voet, J.G., eds., "Chapter 28: Nucleic Acid Structures and Manipulation," in Biochemistry, 1st Ed., John Wiley & Sons, Inc., San Francisco, CA (1990).
Walker, G.T., et al., "Isothermal in vitro amplification of DNA by a restriction enzyme/DNA polymerase system," Proc, Natl. Acad. Sci. US.A. 89:392-396, National Academy of Sciences (1992).
Walker, G.T., et al., "Strand displacement amplification—an isothermal, in vitro DNA amplification technique," Nucleic Acids Res. 20:1691-1696, Oxford University Press (1992).
Gandini et al., "Is DD3 a New Prostate-Specific Gene?," Anticancer Res. 23:305-308, Anticancer Research (Jan.-Feb. 2003).
Gen-Probe Brochure, "Prostate Cancer Gene 3 (PCA3): the new tool available to improve the diagnosis of prostate cancer in a simple urine test", Gen_Probe Incorporated (2007).
Gibson et al., "A novel method for real time quantitative RT-PCR". Genome Res. 6:995-1001 (1996).
Goessl et al., "A DNA-Based Method for Detection of Prostate Cancer Cells in Urine After Prostatic Massage," Eur. Urol. Suppl. 1:32, article 118, Elsevier Science (Jan. 2002).
Goessl et al., "DNA-Based Detection of Prostate Cancer in Urine After Prostatic Massage," Urology 58:335-338, Elsevier Science (Sep. 2001).
Goessl et al., "Fluorescent Methylation-specific Polymerase Chain Reaction for DNA-based Detection of Prostate Cancer in Bodily Fluids," Cancer Res. 60:5941-5945, American Association for Cancer Research (Nov. 2000).
Goldman et al., "Can prostate-specific antigen reverse transcriptase-polymerase chain reaction be used as a prospective test to diagnose prostate cancer?" World J Urol. 15:257-61 (1997).
Gomella et al., "Reverse Transcriptase Polymerase Chain Reaction for Prostate Specific Antigen in the Management of Prostate Cancer," J. Urology 158:326-337, American Urological Association, Inc. (1997).
Gotoh, A., et al., "Development of Prostate-Specific Antigen Promoter-Based Gene Therapy for Androgen-Independent Human Prostate Cancer," J. Urol. 160:220-229, American Urological Association, Inc. (Jul. 1998).
Grasso et al., "Combined nested RT-PCR assay for prostate-specific antigen and prostate-specific membrane antigen in prostate cancer patients: correlation with pathological stage". Cancer Res. 58:1456-9 (1998).
Grayburn and Sims, "Anchored Oligo(dT) Primers for Automated Dye Terminator DNA Sequencing", BioTechniques. 25(3):340-346 (1998).
Gu et al., "Prostate stem cell antigen (PSCA) expression increases with high gleason score, advanced stage and bone metastasis in prostate cancer". Oncogene. 19:1288-96 (2000).
Guichet et al., "The nuclear receptor homologue Ftz-F1 and the homeodomain protein Ftz are mutually dependent cofactors," Nature 385:548-552, Nature Publishing Group (1997).
Hessels, D., et al. "DD3Pcm-based Molecular Urine Analysis for the Diagnosis of Prostate Cancer," Eur. Urol. 44:8-15, Elsevier Science (Jul. 2003).
Hillier and Green, "OSP: A computer program for choosing PCR and DNA sequenceing primers", PCR Methods Appl. 1:124-128 (1991).
Horninger et al., "Complexed prostate-specific antigen for early detection of prostate cancer in men with serum prostate-specific antigen levels of 2 to 4 nanograms per milliliter." Urology. 60(4):31-35 (2002).
Houdebine, L.-M., "Production of pharmaceutical proteins from transgenic animals," J. Biochem. 34:269-287, Oxford University Press (1994).
Hsing, A.W., et al., "International Trends and Patterns of Prostate Cancer Incidence and Mortality," Int J. Cancer 85:60-67, Wiley-Liss, Inc., (Jan. 2000).

(56) References Cited

OTHER PUBLICATIONS

Ingelfinger, R.J., "Nephrogenic Adenomas As Renal Tubular Outposts," N. Engl. J. Med. 347:684-686, Massachusetts Medical Society (Aug. 2002).

Israeli et al., "Sensitive Nested Reverse Transcription Polymerase Chain Reaction Detection of Circulating Prostatic Tumor Cells: Comparison of Prostate-specific Membrane Antigen and Prostatespecific Antigen-based Assays," Cancer Res. 54:6306-6310, American Association for Cancer Research (1994).

Iwakiri, J., et al., "An Analysis of Urinary Prostate Specific Antigen Before and After Radical Prostatectomy: Evidence for Secretion of Prostate Specific Antigen by the Periurethral Glands," J. Urol. 149:783-786, Elsevier Science Ltd. (1993).

Jensen et al., "Cancer in the European Community and its member states". Eur J Cancer 26:1167-256 (1990).

Journal Sentinel wire reports, "Prostate blood test may but down on biopsies", May 20, 1998.

Kamoi K, Babaian RJ. "Advances in the application of prostate-specific antigen in the detection of early-stage prostate cancer". Semin Oncol, 26:140-9 (1999).

Katz et al., "Enhanced reverse transcriptase-polymerase chain reaction for prostate specific antigen as an indicator of true pathologic stage in patients with prostate cancer". Cancer. 75:1642-8 (1995).

Katz et al., "Molecular staging of prostate cancer with the use of an enhanced reverse transcriptase-PCR assay". Urology 1994;43:765-75.

Kirby, R.S., "Pre-treatment staging of prostate cancer: recent advances and future prospects," Prostate Cancer and Prostatic Dis. 1:2-10, Stockton Press (1997).

Kwoh, D.Y., et al., "Transcription-based amplification system and detection of amplified human immunodeficiency virus type 1 with a bead-based sandwich hybridization format," Proc. Natl. Acad. Sci. USA. 86:1173-1177, National Academy of Sciences (1989).

Kwok et al., "A guide to the design and use of mismatched and degenerate primers", PCR Methods Appl. 3:39-47 (1994).

Landis et al., "Cancer Statistics, 1998", CA Cancer J Clin 48(1):6-29 (1998).

Landis et al., "Cancer Statistics, 1999," CA Cancer J. Clin. 49:8-31, Lippincott Williams & Wilkins (Jan.-Feb. 1999).

Lange, P.H., "Chapter 41. Tumor Markers in Prostate Cancer," in: Principles and Practice of Genitourinary Oncology, Raghaven, D. et al., eds., Lippincott-Raven Publishers, Philadelphia, PA, pp. 417-425 (1997).

Lathe, R., "Synthetic Oligonucleotide Probes Deduced from Amino Acid Sequence Data Theoretical and Practical Considerations," J. Mol. Biol. 183:1-12, Academic Press (1985).

Lazar, E., et al., "Transforming growth factor a: mutation of aspartic acid 47 and leucine 48 results in different biological activities," Mol. Cell Biol. 8:1247-1252, American Society for Microbiology (1988).

Letran, J.L. et al., "Repeat Ultrasound Guided Prostate Needle Biopsy: Use of Free-To-Total Prostate Specific Antigen Ratio in Predicting Prostatic Carcinoma," J. Urology 160:426-429, American Urological Association, Inc. (Aug. 1998).

Lin et al., "Prostatelocalized and androgen-regulated expression of the membrane-bound serine protease TMPRSS2". Cancer Res. 59:4180-4 (1999).

Lintula S, Stenman UH. "The expression of prostate-specific membrane antigen in peripheral blood leukocytes". J Urol. 157:1969-72 (1997).

Lizardi, P., et al., "Exponential Amplification of Recombinant-RNA Hybridization Probes," BioTechnology 6:1197-1202, Nature Publishing Group (1988).

Lowe et al., "A computer program for selection of oligonucleotide primers for polymerase chain reactions", Nucleic Acids Research. 18(7):1757-1761 (1990).

Malek, L., et al., "Nucleic Acid Sequence-Based Amplification (NASBA)," Methods Mol. Biol. 28:253-260, Humana Press (1994).

Marks et al., "PCA3 molecular urine assay for prostate cancer in men undergoing repeat biopsy", Adult Urology, 69 (3):532-535(2007).

Martiniello-Wilks, R., et al.,"In Vivo Gene Therapy for Prostate Cancer: Preclinical Evaluation of Two Different Enzyme-Directed Prodrug Therapy Systems Delivered by Identical Adenovirus Vectors," Hum. Gene Ther. 9:1617-1626, Maty Ann Liebert, Inc. (Jul. 1998).

Matteucci, M.D., and Caruthers, M.H., "Synthesis of Deoxyoligonucleotides on a Polymer Support," J. Am. Chem. Soc. 103:3185-3191, American Chemical Society (1981).

Merriam-Webster Online Dictionary, definition for "kit" (Accessed Dec. 2005).

Mettlin et al., "The National Cancer Data Base report on longitudinal observations on prostate cancer". Cancer 77:2162-6 (1996).

Miller, P.S., and Ts'o, P.O.P., "Chapter 30: Oligonucleotide Inhibitors of Gene Expression in Living Cells: New Opportunities in Drug Design," Annu. Rep. Med, Chem. 23:295-304, Academic Press (1988).

Millikan, R.E., "Chemotherapy of Advanced Prostatic Carcinoma," Semin. Oncol. 26:185-191, W.B. Saunders Company (Apr. 1999).

Mintun et al., "Increased lactate pyruvate ratio augments blood flow in physiologically activated human brain", 101 (2):659-664 (2004).

Morvan, F., et al., "a-DNA. L Synthesis, characterization by high field III-NMR, and base-pairing properties of the unnatural hexadeoxyribonucleotide a-[d(CpCpTpTpCpC)] with its complement P-[d(GpGpApApGpG)]," Nucleic Acids Res. 14:5019-5035, Oxford University Press (1986).

Muller and Brenner, "Urine Markers as Possible Tools for Prostate Cancer Screening: Review of Performance Characteristics and Practicality", Clinical Chemistry, 524:562-573 (2006).

Goessl et al., "DNA-Based Detection of Prostate Cancer in Blood, Urine, and Ejaculates," *Ann NY Acad. Sci.* 945:51-58, 2001.

```
CON 61   GAAGATCTGC ATGGTGGGAA GGACCTGATG ATACAGAGGA ATTACAACAC ATATACTTAG 2   23   tgtttcaatg aacaccaaga taaataagtg aagagctagt ccgctgtgag tctcctcagt

CON 121  TGTTTCAATG AACACCAAGA TAAATAAGTG AAGAGCTAGT CCGCTGTGAG TCTCCTCAGT 2   83   gacacagggc tggatcacca tcgacggcac tttctgagta ctcagtgcag caaagaaag

CON 181  GACACAGGGC TGGATCACCA TCGACGGCAC TTTCTGAGTA CTCAGTGCAG CAAAGAAAG 2  142   actacagaca tctcaatggc aggg
3    1                            gtgaga aataagaaag gctgctgact ttaccatctg

CON 240  ACTACAGACA TCTCAATGGC AGGGGTGAGA AATAAGAAAG GCTGCTGACT TTACCATCTG 3   37   aggccacaca tctgctgaaa tggagataat taacatcact agaaacagca agatgacaat

CON 300  AGGCCACACA TCTGCTGAAA TGGAGATAAT TAACATCACT AGAAACAGCA AGATGACAAT
```

FIG. 2C

```
3    97                ataatgtcta agtagtgac atgttttttg cacatttcc agcccctttt aaatatcca cacaca CON  360               ATAATGTCTA AGTAGTGAC ATGTTTTTG CACATTTCC AGCCCCTTT AAATATCCA CACACA
PCA3   1                              M  F  L   H  I  S   S  P  F   K  Y  P   H  T 3   158                caggaagca caaaaggaa gcacagag
4     1                                            a tccctggga gaaatgccc ggccgccat cttggg CON  421               CAGGAAGCA CAAAAGGAA GCACAGAGA TCCCTGGGA GAAATGCCC GGCCGCCAT CTTGGG
PCA3  15                Q  E  A   Q  K  E   A  Q  R   S  L  G   E  M  P   G  R  H   L  G 4    35                tcatcgatg agcctcgcc ctgtgcctg gtcccgctt gtgAGGGAA GGACATTAG AAA CON  481               TCATCGATG AGCCTCGCC CTGTGCCTG GTCCCGCTT GTGAGGGAA GGACATTAG AAA
PCA3  35                S  S  M   S  L  A   L  C  L   V  P  L   V  R  E   G  H  ***

4    93                ATGAATTGAT GTGTTCCTTA AAGGATGGGC AGGAAAACAG ATCCTGTTGT GGATATTTAT

CON  538               ATGAATTGAT GTGTTCCTTA AAGGATGGGC AGGAAAACAG ATCCTGTTGT GGATATTTAT
```

Fig. 2D

```
4    153  TTGAACGGGA TTACAGATTT GAAATGAAGT CACAAAGTGA GCATTACCAA TGAGAGGAAA

CON  598  TTGAACGGGA TTACAGATTT GAAATGAAGT CACAAAGTGA GCATTACCAA TGAGAGGAAA 4    213  ACAGACGAGA AAATCTTGAT GGCTTCACAA GACATGCAAC AAACAAAATG GAATACTGTG

CON  658  ACAGACGAGA AAATCTTGAT GGCTTCACAA GACATGCAAC AAACAAAATG GAATACTGTG 4    273  ATGACATGAG GCAGCCAAGC TGGGGaggag ataaccacgg ggcaGAGGGT CAGGATTCTG

CON  718  ATGACATGAG GCAGCCAAGC TGGGGGAGGAG ATAACCACGG GGCAGAGGGT CAGGATTCTG 4    333  GCCCTGCTGC CTAAACTGTG CGTTCATAAC CAAATCATTT CATATTTCTA ACCCTCAAAA

CON  778  GCCCTGCTGC CTAAACTGTG CGTTCATAAC CAAATCATTT CATATTTCTA ACCCTCAAAA
```

FIG. 2E

```
4    393   CAAAGCTGTT GTAATATCTG ATCCTCTACGG TTCCTTCTGG GCCCAACATT CTCCATATAT
CON  838   CAAAGCTGTT GTAATATCTG ATCCTCTACGG TTCCTTCTGG GCCCAACATT CTCCATATAT 4    453   CCAGCCACAC TCATTTTTAA TATTTAGTTC CCAGATCTGT ACTGTGACCT TTCTACACTG
CON  898   CCAGCCACAC TCATTTTTAA TATTTAGTTC CCAGATCTGT ACTGTGACCT TTCTACACTG 4    513   TAGAATAACA TTACTCATTT TGTTCAAA
5      1                               GA CCCTTCGTGT TGCTGCCTAA TATGTAGCTG
CON  958   TAGAATAACA TTACTCATTT TGTTCAAAGA CCCTTCGTGT TGCTGCCTAA TATGTAGCTG 5     33   ACTGTTTTTC CTAAGGAGTG TTCTGGCCCA GGGGATCTGT GAACAGGCTG GGAAGCATCT
CON 1018   ACTGTTTTTC CTAAGGAGTG TTCTGGCCCA GGGGATCTGT GAACAGGCTG GGAAGCATCT 5     93   CAAGATCTTT CCAGGGTTAT ACTTACTAGC ACACAGCATG ATCATTACGG AGTGAATTAT
```

Fig. 2F

```
CON  1078  CAAGATCTTT  CCAGGGTTAT  ACTTACTAGC  ACACAGCATG  ATCATTACGG  AGTGAATTAT
5     153  CTAATCAACA  TCATCCTCAG  TGTCTTTGCC  CATACTGAAA  TTCATTCCCC  ACTTTTGTGC
CON  1138  CTAATCAACA  TCATCCTCAG  TGTCTTTGCC  CATACTGAAA  TTCATTCCCC  ACTTTTGTGC
5     213  CCATTCTCAA  GACCTCAAAA  TGTCATTCCA  TTAATATCAC  AGGATTAACT  TTTTTTTTTA
CON  1198  CCATTCTCAA  GACCTCAAAA  TGTCATTCCA  TTAATATCAC  AGGATTAACT  TTTTTTTTA
5     273  ACCTGGAAGA  ATTCAATGTT  ACATGCAGCT  ATGGGAATTT  AATTACATAT  TTTGTTTTCC
CON  1258  ACCTGGAAGA  ATTCAATGTT  ACATGCAGCT  ATGGGAATTT  AATTACATAT  TTTGTTTTCC
5     333  AGTGCAAAGA  TGACTAAGTC  CTTTATCCCT  CCCCTTTGTT  TGATTTTTTT  TCCAGTATAA
CON  1318  AGTGCAAAGA  TGACTAAGTC  CTTTATCCCT  CCCCTTTGTT  TGATTTTTTT  TCCAGTATAA
```

FIG. 2G

```
5    393   AGTTAAAATG CTTAGCCTTG TACTGAGGCT GTATACAGCA CAGCCTCTCC CCATCCCTCC
CON  1378  AGTTAAAATG CTTAGCCTTG TACTGAGGCT GTATACAGCA CAGCCTCTCC CCATCCCTCC 5    453   AGCCTTATCT GTCATCACCA TCAACCCCTC CCATNYSACC TAAACAAAAT CTAACTTGTA
CON  1438  AGCCTTATCT GTCATCACCA TCAACCCCTC CCATNYSACC TAAACAAAAT CTAACTTGTA 5    513   ATTCCTTGAA CATGTCAGGN CATACATTRT TCCTTCTGCC TGAGAAGCTC TTCCTTGTCT
CON  1498  ATTCCTTGAA CATGTCAGGN CATACATTRT TCCTTCTGCC TGAGAAGCTC TTCCTTGTCT 5    573   CTTAANTCTA GAATGATGTA AAGTTTTGAA TAAGTTGACT ATCTTACTTC ATGCAAAGAA
CON  1558  CTTAANTCTA GAATGATGTA AAGTTTTGAA TAAGTTGACT ATCTTACTTC ATGCAAAGAA
```

FIG. 2H

```
5    633   GGGACACATA  TGAGATTCAT  CATCACATGA  GACAGCAAAT  ACTAAAAGTG  TAATTTGATT

CON  1618  GGGACACATA  TGAGATTCAT  CATCACATGA  GACAGCAAAT  ACTAAAAGTG  TAATTTGATT 5    693   ATAAGAGTTT  AGATAAATAT  ATGAAATGCA  AGAKCCACAG  AGGGAATGTT  TATGGGGCAC

CON  1678  ATAAGAGTTT  AGATAAATAT  ATGAAATGCA  AGAKCCACAG  AGGGAATGTT  TATGGGGCAC 5    753   GTTTGTAAGC  CTGGGATGTG  AAGMAAAGGC  AGGGAACCTC  ATAGTATCTT  ATATAATATA

CON  1738  GTTTGTAAGC  CTGGGATGTG  AAGMAAAGGC  AGGGAACCTC  ATAGTATCTT  ATATAATATA 5    813   CTTCATTTCT  CTATCTCTAT  CACAATATCC  AACAAGCTTT  TCACAGAATT  CATGCAGTGC

CON  1798  CTTCATTTCT  CTATCTCTAT  CACAATATCC  AACAAGCTTT  TCACAGAATT  CATGCAGTGC 5    873   AAATCCCCAA  AGGTAACCTT  TATCCATTTC  ATGGTGAGTG  CGCTTTAGAA  TTTGGCAAA
```

FIG. 21

```
CON  1858  AAATCCCCAA AGTAAACCTT TATCCATTTC ATGGTGAGTG CGCTTTAGAA TTTTGGCAAA 5     933  TCATACTGGT CACTTATCTC AACTTTGAGA TGTGTTTGTC CTTGTAGTTA ATTGAAAGAA
CON  1918  TCATACTGGT CACTTATCTC AACTTTGAGA TGTGTTTGTC CTTGTAGTTA ATTGAAAGAA 5     993  ATAGGGCACT CTTgtgagcc actttagggt tcactcctgg caataaagaa tttacaaaga
CON  1978  ATAGGGCACT CTTgtgagcc actttagggt tcactcctgg caataaagaa tttacaaaga
```

FIG. 2J

PCA3 cDNA clones
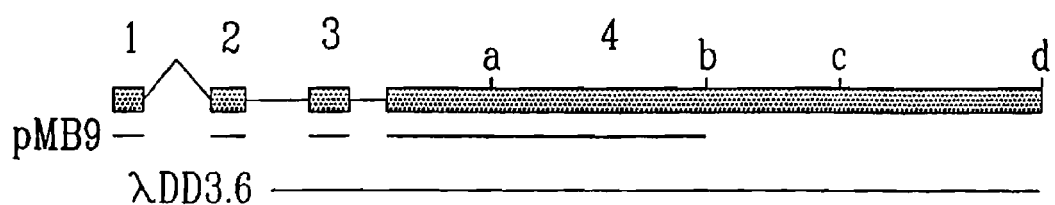
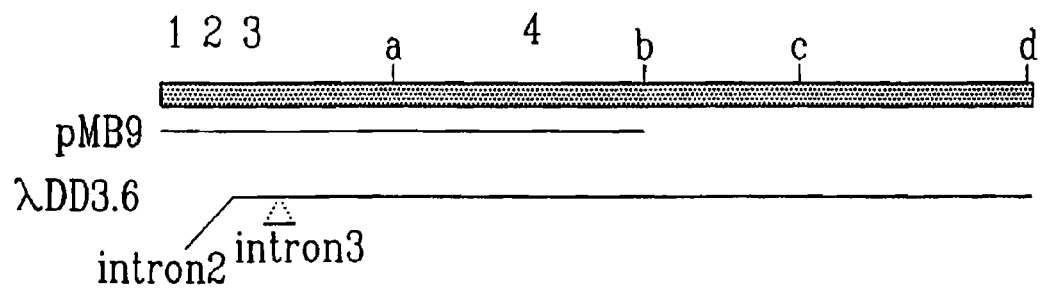
FIG. 3

```
       286
       285
121    469    1008                    2067         2623
120    468    1007                    2066         2622      3582
===================================================================
>E1>E2>E3->-EXON-4A->-----EXON-4B-----> ---EXON-4C-> ----EXON-4D-----> 
                                >PCA3>
1|---------------------------------------------------------------|3582
       401    553
```

FIG. 5A

Sequence PCA3 cDNA and PCA3 protein:

```
  1  ACAGAAGAAA TAGCAAGTGC CGAGAAGCTG GCATCAGAAA AACAGAGGGG AGATTTGTGT
 61  GGCTGCAGCC GAGGGAGACC AGGAAGATCT GCATGGTGGG AAGGACCTGA TGATACAGAG
121  GAATTACAAC ACATATACTT AGTGTTTCAA TGAACACCAA GATAAATAAG TGAAGAGCTA
181  GTCCGCTGTG AGTCTCCCTCA GTGACACAGG GCTGGATCAC CATCGACGGC ACTTTCTGAG
241  TACTCAGTGC AGCAAAGAAA GACTACAGAC ATCTCAATGG CAGGGGTGAG AAATAAGAAA
301  GGCTGCTGAC TTTACCATCT GAGGCCACAC ATCTGCTGAA ATGGAGATAA TTAACATCAC
```

FIG. 5B

```
 361       TAGAAACAGC AAGATGACAA TATAATGTCT AAGTAGTGAC ACAAAAGGAA TATAATGTCT AAGTAGTGAC ACATTTCCAG
PCA3 1                                                                                    S

421       CCCCTTTAAA TATCCACACA CACAGGAAGC ACAAAAGGAA GCACAGAGAT CCCTGGGAGA
PCA3 8      P  F  K    Y  P  H    T  Q  E  A   Q  K  E    A  Q  R    S  L  G  E

481       AATGCCCGGC CGCCATCTTG GGTCATCGAT GAGCCTCGCC CTGTGCCTTG TCCCGCTTGT
PCA3 28     M  P  G    R  H  L    G  S  S  M   S  L  A    L  C  L    V  P  L  V

541       GAGGGAAGGA CATTAGAAAA TGAATTGATG TGTTCCTTAA AGGATGGGCA GGAAAACAGA
PCA3 48     R  E  G    H  *

601       TCCTGTGTTG GATATTTATT TGAACGGGAT TACAGATTTG AAATGAAGTC ACAAAGTGAG

661       CATTACCAAT GAGAGGAAAA CAGACGAGAA AATCTTGATG GCTTCACAAG ACATGCAACA

721       AACAAAATGG AATACTGTGA TGACATGAGG CAGCCAAGCT GGGGAGGAGA TAACCACGGG

781       GCAGAGGGTC AGGATTCTGG CCCTGCTGCC TAAACTGTGC GTTCATAACC AAATCATTTC

841       ATATTTCTAA CCCTCAAAAC AAAGCTGTTG TAATATCTGA TCTCTACGGT TCCTTCTGGG

901       CCCAACATTC TCCATATATC CAGCCACACT CATTTTTAAT GCTTCACAAG CAGATCTGTA

961       CTGTGACCTT TCTACACTGT AGAATAACAT TACTCATTTT GTTCAAAGAC CCTTCGTGTT

1021       GCTGCCTAAT ATGTAGCTGA CTGTTTTTCC TAAGGAGTGT TCTGGCCCAG GGGATCTGTG
```

FIG. 5C

```
1081  AACAGGCTGG  GAAGCATCTC  AAGATCTTTC  CAGGGTTATA  CTTACTAGCA  CACAGCATGA
1141  TCATTACGGA  GTGAATTATC  TAATCAACAT  CATCCCTCAGT GTCTTTGCCC  ATACTGAAAT
1201  TCATTTCCCA  CTTTTGTGCC  CATTCTCAAG  ACCTCAAAAT  GTCATTCCAT  TAATATCACA
1261  GGATTAACTT  TTTTTTTTAA  CCTGGAAGAA  TTCAATGTTA  CATGCAGCTA  TGGGAATTTA
1321  ATTACATATT  TTGTTTTCCA  GTGCAAAGAT  GACTAAGTCC  TTTATCCCTC  CCCTTTGTTT
1381  GATTTTTTT   CCAGTATAAA  GTTAAAAATGC TTAGCCTTGT ACTGAGGCTG  TATACAGCAC
1441  AGCCTCTCCC  CATCCCTCCA  GCCTTATCTG  TCATCACCAT  CAACCCCTCC  CATACCACCT
1501  AAACAAAATC  TAACTTGTAA  TTCCTTGAAC  ATGTCAGGAC  ATACATTATT  CCTTCTGCCT
1561  GAGAAGCTCT  TCCTTGTCTC  TTAAATCTAG  AATGATGTAA  AGTTTTGAAT  AAGTTGACTA
1621  TCTTACTTCA  TGCAAAGAAG  GGACACATAT  GAGATTCATC  ATCACATGAG  ACAGCAAATA
1681  CTAAAAGTGT  AATTTGATTA  TAAGAGTTTA  GATAAATATA  TGAAATGCAA  GAGCCACAGA
1741  GGGAATGTTT  ATGGGGCACG  TTTGTAAGCC  TGGGATGTGA  AGCAAAGGCA  GGGAACCTCA
1801  TAGTATCTTA  TATAATATAC  TTCATTTCTC  TATCTCTATC  ACAATATCCA  ACAAGCTTTT
1861  CACAGAATTC  ATGCAGTGCA  AATCCCCAAA  GGTAACCTTT  ATCCATTTCA  TGGTGAGTGC
```

FIG. 50

```
1921  GCTTTAGAAT TTTGGCAAAT CATACTGGTC ACTTATCTCA ACTTTGAGAT GTGTTTGTCC
1981  TTGTAGTTAA TTGAAAGAAA TAGGGCACTC TTGTGAGCCA CTTTAGGGTT CACTCCTGGC
2041  AATAAAGAAT TTACAAAGAG CTACTCAGGA CCAGTTGTTA AGAGCTCTGT GTGTGTGTGT
2101  GTGTGTGTGT GAGTGTACAT GCCAAAGTGT GCCTCTCTCT CTTGACCCAT TATTTCAGAC
2161  TTAAAACAAG CATGTTTTCA AATGGCACTA TGAGCTGCCA ATGATGTATC ACCACCATAT
2221  CTCATTATTC TCCAGTAAAT GTGATAATAA TGTCATCTGT TAACATAAAA AAAGTTTGAC
2281  TTCACAAAAG CAGCTGGAAA TGGACAACCA CAATATGCAT AAATCTAACT CCTACCATCA
2341  GCTACACACT GCTTGACATA TATTGTTAGA AGCACCTCGC ATTTGTGGGT TCTCTTAAGC
2401  AAAATACTTG CATTAGGTCT CAGCTGGGGC TGTGCATCAG GCGGTTTGAG AAATATTCAA
2461  TTCTCAGCAG AAGCCAGAAT TTGAATTCCC TCATCTTTTA GGAATCATTT ACCAGGTTTG
2521  GAGAGGATTC AGACAGCTCA GGTGCTTTCA CTAATGTCTC TGAACTTCTG TCCCTCTTTG
2581  TGTTCATGGA TAGTCCAATA AATAATGTTA TCTTTGAACT GATGCTCATA GGAGAGAATA
2641  TAAGAACTCT GAGTGATATC AACATTAGGG ATTCAAAGAA ATATTAGATT TAAGCTCACA
2701  CTGGTCAAAA GGAACCAAGA TACAAAGAAC TCTGAGCTGT CATCGTCCCC ATCTCTGTGA
```

FIG. 5E

```
2761  GCCACAACCA ACAGCAGGAC CCAACGCATG TCTGAGATCC TTAAATCAAG GAAACCAGTG
2821  TCATGAGTTG AATTCTCCTA TTATGGATGC TAGCTTCTGG CCATCTCTGG CTCTCCTCTT
2881  GACACATATT AGCTTCTAGC CTTTGCTTCC ACGACTTTTA TCTTTTCTCC AACACATCGC
2941  TTACCAATCC TCTCTCTGCT CTGTTGCTTT GGACTTCCCC ACAAGAATTT CAACGACTCT
3001  CAAGTCTTTT CTTCCATCCC CACCACTAAC CTGAATTGCC TAGACCCTTA TTTTTATTAA
3061  TTTCCAATAG ATGCTGCCTA TGGGCTAATA TTGCTTTAGA TGAACATTAG ATATTTAAAG
3121  TCTAAGAGGT TCAAAAATCCA ACTCATTATC TTCTCTTTCT TTCACCTCCC CTGCTCCTCT
3181  CCCTATATTA CTGATTGACT GAACAGGATG GTCCCCAAGA TGCCAGTCAA ATGAGAAACC
3241  CAGTGGCTCC TTGTGGATCA TGCATGCAAG ACTGCTGAAG CCAGAGGATG ACTGATTACG
3301  CCTCATGGGT GGAGGGGACC ACTCCCTGGG CTTCGTGATT GTCAGGAGCA AGACCTGAGA
3361  TGCTCCCTGC CTTCAGTGTC CTCTGCATCT CCCCTTTCTA ATGAAGATCC ATAGAATTTG
3421  CTACATTTGA GAATTCCAAT TAGGAACTCA CATGTTTTAT CTGCCCTATC AATTTTTTAA
3481  ACTTGCTGAA AATTAAGTTT TTTCAAAAATC TGTCCTTGTA AATTACTTTT TCTTACAGTG
3541  TCTTGGCATA CTATATCAAC TTTGATTCTT TGTTACAACT TT
```

FIG. 5F

PCA3, PCA3 GENES, AND METHODS OF USE

CROSS REFERENCE TO RELATED APPLICATIONS

This application is a continuation application of recently allowed U.S. application Ser. No. 11/260,282 filed on Oct. 28,2005, now U.S. Pat. No. 7,632,643, which itself is a divisional of U.S. patent application Ser. No. 09/402,713 filed on Jun. 13,2000, now U.S. Pat. No. 7,008,765 and which claims priority on international Application Number PCT/CA98/000346 filed Apr. 9, 1998, which itself claims priority on U.S. provisional application Ser. No. 60/041,836 filed Apr. 10, 1997. The patent applications identified above are incorporated here by reference in their entirety to provide continuity of disclosure.

STATEMENT REGARDING FEDERALLY-SPONSORED RESEARCH AND DEVELOPMENT

Statement under MPEP 310. The U.S. government has a paid-up license in this invention and the right in limited circumstances to require the patent owner to license others on reasonable terms as provided for by the terms of Grant No. CA 58236 awarded by the U.S. Department of Health and Human Services National Institutes of Health.
Part of the work performed during development of this invention utilized U.S. Government funds. The U.S. Government has certain rights in this invention.

FIELD OF THE INVENTION

The present invention relates, in general, to a prostate cancer antigen, PCA3. In particular, the present invention relates to nucleic acid molecules coding for the PCA3 protein; purified PCA3 proteins and polypeptides; recombinant nucleic acid molecules; cells containing the recombinant nucleic acid molecules; antibodies having binding affinity specifically to PCA3 proteins and polypeptides; hybridomas containing the antibodies; nucleic acid probes for the detection of nucleic acids encoding PCA3 proteins; a method of detecting nucleic acids encoding PCA3 proteins or polypeptides in a sample; kits containing nucleic acid probes or antibodies; bioassays using the nucleic acid sequence, protein or antibodies of this invention to diagnose, assess, or prognose a mammal afflicted with prostate cancer; therapeutic uses; and methods of preventing prostate cancer in an animal.

SEQUENCE LISTING

This application contains a Sequence Listing in computer readable form entitled "Sequence Listing", created Oct. 23, 2009, having a size of 14.4 Ko. The computer readable form is incorporated herein by reference.

BACKGROUND OF THE INVENTION

Prostate cancer is the most commonly diagnosed malignancy and the second leading cause of cancer-related deaths in the western male population. When this carcinoma has locally or distantly spread, no curative therapy can be offered. Therefore, efforts to control the disease (i.e., to decrease prostate cancer mortality) have focused on increasing detection of the cancer while it is still locally confined and potentially curable. Studies aimed at the early detection of prostate cancer have demonstrated an appreciable increase in the detection of organ-confined potentially curable prostate cancers. However, it has not yet been demonstrated that the increased detection rate will decrease the prostate cancer-specific mortality rates. On the other hand, there is also no evidence that early diagnosis will decrease the mortality rates. Both in the United States and in Europe, discussions on the efficacy and acceptability of screening programs, the issue of overdiagnosis and overtreatment and the chances that early treatment will lead to reduced prostate cancer morbidity and mortality, are still ongoing and make early detection of prostate cancer a controversial issue (Schröder, *Urology* 46: 6270 (1995)).

Measurements of serum concentrations of prostatic marker enzymes have recognized value in the clinical detection, diagnosis and management of prostate cancer. The two most widely used prostatic marker enzymes are prostatic acid phosphatase (PAP) and prostate-specific antigen (PSA). Normally, both enzymes are secreted from the prostatic epithelial cells into the seminal fluid, but in patients with prostatic disease they leak into the circulation, where they can be detected by means of immunological assays (Armbruster, *Clin. Che.* 39: 181-95 (1993)).

Prostatic acid phosphatase, one of the earliest serum markers for prostate, has an as yet undetermined function and is one of the most predominant protein components in human prostatic secretions. The use of PAP as a marker for prostatic tumors is complicated by the reported structural similarities between the prostate-specific acid phosphatase and the lysosomal acid phosphatase occurring in all tissues. Furthermore, there is a tendency towards lower PAP mRNA and protein levels in prostate cancer in comparison with benign prostatic hyperplasia (BPH). In recent years, PAP measurements were superseded by serum PSA measurements in the clinical management of prostate cancer.

Prostate-specific antigen was identified by several groups in the 1970's as a prostate-specific protein from the seminal fluid. In 1979, it was purified as an antigen from prostate cancer tissue. Further research showed that PSA is produced exclusively by the columnar epithelial cells of the prostate and periuretural glands. Normal prostate epithelium and benign hyperplastic tissue actually produce more PSA mRNA and protein than does prostate cancer tissue. Furthermore, it was shown that loss of differentiation of prostatic carcinomas is associated with a decrease in the level of intraprostatic PSA.

Abnormalities in prostate architecture occurring as a result of prostatic disease lead to an increased leakage of PSA (and PAP) into the serum and make serum PSA measurements a marker for prostate cancer. Despite the fact that early studies have indicated that diagnostic PSA testing would be hampered by the fact that it lacked specificity in differentiating between BPH and prostate cancer, PSA testing was introduced in 1986 and revolutionized the management of patients with prostate cancer. Increased knowledge on the organ specificity of PSA and the relationship of elevated serum PSA levels to prostate disease as well as improvement of biopsy techniques and histological evaluation, led to a appreciation of the clinical value of PSA testing, a utility not yet achieved by any other (prostate) tumor marker. Cloning of the gene that encodes PSA revealed that it is a member of the human kallikrein gene family and resulted in the development of new approaches to the use of PSA as a marker: the very sensitive reverse transcriptaske polymerase chain reaction (RT-PCR) method is used to detect extremely small numbers of malignant prostate cells in blood samples from prostate cancer patients and might provide a sensitive tool to identify patients with micrometastatic disease (Moreno et al., *Cancer Res.* 52: 6110-12 (1992); and Katz et al., *Urology* 43: 765-75 (1994)).

Prostate-specific membrane antigen (PSM) was originally identified using an antibody developed by immunizing mice with the membrane fraction of LNCaP human prostatic adenocarcinoma cells. Like PAP and PSA, PSM can be detected in normal prostate, BPH and prostate cancer and is absent from most other tissues. Also for PSM, RT-PCR studies have been developed to detect circulating prostate cancer cells, however, further investigations are required to establish the usefulness of PSM as marker for prostatic cancer.

In summary, PSA is currently recognized as the premier marker for prostatic cancer, being useful for screening selected populations of patients with symptoms indicative of prostate cancer and for monitoring patients after therapy, especially after surgical prostatectomy (measurable levels of PSA indicate residual disease or metastasis and increasing PSA concentrations indicate recurrent disease). The significant weaknesses of PSA as a tumor marker are that (1) PSA is not able to always distinguish prostate cancer from BPH; and (2) that its expression decreases with loss of differentiation of carcinomas.

In view of the fact that advanced prostate cancer remains a life threatening disease reaching a very significant proportion of the male population, there remains a need for the development of new treatment and diagnostic modalities for (late stage) prostate cancer.

The present invention seeks to meet these and other needs.

The present description refers to a number of documents, the contents of which are herein incorporated in their entirety by reference.

SUMMARY OF THE INVENTION

The invention provides, in general, isolated nucleic acid molecules coding for PCA3 or fragments thereof.

The invention further provides purified polypeptides encoding PCA3 or an epitope binding portion thereof.

The invention also provides nucleic acids for the specific detection of the presence of nucleic acids encoding PCA3 proteins or polypeptides in a sample.

The invention further provides a method of detecting nucleic acid encoding PCA3 in a sample.

The invention also provides a kit for detecting the presence of nucleic acid encoding PCA3 in a sample.

The invention further provides a recombinant nucleic acid molecule comprising, 5' to 3', a promoter effective to initiate transcription in a host cell and the above-described isolated nucleic acid molecule.

The invention also provides a recombinant nucleic acid molecule comprising a vector and the above-described isolated nucleic acid molecule.

The invention further provides an antisense PCA3 nucleic acid molecule.

The invention also provides a cell that contains the above-described recombinant nucleic acid molecule.

The invention further provides a non-human organism that contains the above-described recombinant nucleic acid molecule.

The invention also provides an antibody having binding affinity specifically to PCA3 or an epitope-bearing portion thereof.

The invention further provides a method of detecting PCA3 in a sample.

The invention also provides a method of measuring the amount of PCA3 in a sample.

The invention in addition provides immunogenic reagents to induce protection against PCA3-expressing prostate cancer cells. Preferably, such immunogenic reagents are polypeptides encoding PCA3, an antigenic portion thereof, fusion proteins encoding PCA3 or fusion protein encoding antigenic portions of PCA3. In such an embodiment, these immunogenic reagents would function as vaccine agents.

The invention further provides a method of detecting antibodies having binding affinity specifically to PCA3.

The invention further provides a diagnostic kit comprising a first container means containing the above-described antibody, and a second container means containing a conjugate comprising a binding partner of the monoclonal antibody and a label.

The invention also provides a hybridoma which produces the above-described monoclonal antibody.

The invention further provides diagnostic methods for human disease, in particular, prostate cancer. Preferably, a method of diagnosing the presence or predisposition to develop prostate cancer in a patient is provided herein.

The invention also provides methods for therapeutic uses involving all or part of (1) a nucleic acid sequence encoding PCA3, (2) antisense PCA3 nucleic acid molecules, (2) PCA3 protein, or (4) PCA3 antibodies.

Further objects and advantages of the present invention will be clear from the description that follows.

DEFINITIONS

In the description that follows, a number of terms used in recombinant DNA (rDNA) technology are extensively utilized. In order to provide a clear and consistent understanding of the specification and claims, including the scope to be given such terms, the following definitions are provided.

Isolated Nucleic Acid Molecule. An "isolated nucleic acid molecule", as is generally understood and used herein, refers to a polymer of nucleotides, and includes but should not be limited to DNA and RNA. The "isolated" nucleic acid molecule is purified from its natural in vivo state.

Recombinant DNA. Any DNA molecule formed by joining DNA segments from different sources and produced using recombinant DNA technology (aka. molecular genetic engineering).

DNA Segment. A DNA segment, as is generally understood and used herein, refers to a molecule comprising a linear stretch of nucleotides wherein the nucleotides are present in a sequence that can encode, through the genetic code, a molecule comprising a linear sequence of amino acid residues that is referred to as a protein, a protein fragment or a polypeptide.

Gene. A DNA sequence related to a single polypeptide chain or protein, and as used herein includes the 5' and 3' untranslated ends. The polypeptide can be encoded by a full-length sequence or any portion of the coding sequence, so long as the functional activity of the protein is retained.

Complementary DNA (cDNA). Recombinant nucleic acid molecules synthesized by reverse transcription of messenger RNA ("mRNA").

Structural Gene. A DNA sequence that is transcribed into mRNA that is then translated into a sequence of amino acids characteristic of a specific polypeptide.

Restriction Endonuclease. A restriction endonuclease (also restriction enzyme) is an enzyme that has the capacity to recognize a specific base sequence (usually 4, 5, or 6 base pairs in length) in a DNA molecule, and to cleave the DNA molecule at every place where this sequence appears. For example, EcoRI recognizes the double-stranded palindromic base sequence 5'-GAATTC-3'/3'-CTTAAG-5'.

Restriction Fragment. The DNA molecules produced by digestion with a restriction endonuclease are referred to as restriction fragments. Any given genome can be digested by a particular restriction endonuclease into a discrete set of restriction fragments.

Agarose Gel Electrophoresis. To detect a polymorphism in the length of restriction fragments, an analytical method for fractionating double-stranded DNA molecules on the basis of size is required. The most commonly used technique (though not the only one) for achieving such a fractionation is agarose gel electrophoresis. The principle of this method is that DNA molecules migrate through the gel as though it were a sieve that retards the movement of the largest molecules to the greatest extent and the movement of the smallest molecules to the least extent. Note that the smaller the DNA fragment, the greater the mobility under electrophoresis in the agarose gel.

The DNA fragments fractionated by agarose gel electrophoresis can be visualized directly by a staining procedure if the number of fragments included in the pattern is small. The DNA fragments of genomes can be visualized successfully. However, most genomes, including the human genome, contain far too many DNA sequences to produce a simple pattern of restriction fragments. For example, the human genome is digested into approximately 1,000,000 different DNA fragments by EcoRI. In order to visualize a small subset of these fragments, a methodology referred to as the Southern hybridization procedure can be applied.

Southern Transfer Procedure. The purpose of the Southern transfer procedure (also referred to as blotting) is to physically transfer DNA fractionated by agarose gel electrophoresis onto a nitrocellulose filter paper or another appropriate surface or method, while retaining the relative positions of DNA fragments resulting from the fractionation procedure. The methodology used to accomplish the transfer from agarose gel to nitrocellulose involves drawing the DNA from the gel into the nitrocellulose paper by capillary action.

Nucleic Acid Hybridization. Nucleic acid hybridization depends on the principle that two single-stranded nucleic acid molecules that have complementary base sequences will reform the thermodynamically favored double-stranded structure if they are mixed under the proper conditions. The double-stranded structure will be formed between two complementary single-stranded nucleic acids even if one is immobilized on a nitrocellulose filter. In the Southern hybridization procedure, the latter situation occurs. As noted previously, the DNA of the individual to be tested is digested with a restriction endonuclease, fractionated by agarose gel electrophoresis, converted to the single-stranded form, and transferred to nitrocellulose paper, making it available for reannealing to the hybridization probe. Examples of hybridization conditions can be found in Ausubel, F. M. et al., Current protocols in Molecular Biology, John Wily & Sons, Inc., New York, N.Y. (1989). A nitrocellulose filter is incubated overnight at 68° C. with labeled probe in a solution containing 50% formamide, high salt (either 5×SSC[20×: 3M NaCl/0.3M trisodium citrate] or 5×SSPE [20×: 3.6M NaCl/0.2M $NaH_2PO_4$/0.02M EDTA, pH 7.7]), 5×Denhardt's solution, 1% SDS, and 100 µg/ml denatured salmon sperm DNA. This is followed by several washes in 0.2×SSC/0.1% SDS at a temperature selected based on the desired stringency: room temperature (low stringency), 42° C. (moderate stringency) or 68° C. (high stringency). The temperature selected is determined based on the melting temperature (Tm) of the DNA hybrid.

Hybridization Probe. To visualize a particular DNA sequence in the Southern hybridization procedure, a labeled DNA molecule or hybridization probe is reacted to the fractionated DNA bound to the nitrocellulose filter. The areas on the filter that carry DNA sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide can be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification Primer. An oligonucleotide which is capable of annealing adjacent to a target sequence and serving as an initiation point for DNA synthesis when placed under conditions in which synthesis of a primer extension product which is complementary to a nucleic acid strand is initiated.

Antisense nucleic acid molecule. An "antisense nucleic acid molecule" refers herein to a molecule capable of forming a stable duplex or triplex with a portion of its targeted nucleic acid sequence (DNA or RNA). The use of antisense nucleic acid molecules and the design and modification of such molecules is well known in the art as described for example in WO 96/32966, WO 96/11266, WO 94/15646, WO 93/08845, and U.S. Pat. No. 5,593,974. Antisense nucleic acid molecules according to the present invention can be derived from the nucleic acid sequences of the present invention and modified in accordance to well known methods. For example, some antisense molecules can be designed to be more resistant to degradation, to increase their affinity to their targeted sequence, to affect their transport to chosen cell types or cell compartments, and/or to enhance their lipid solubility by using nucleotide analogs and/or substituting chosen chemical fragments thereof, as commonly known in the art.

Vector. A plasmid or phage DNA or other DNA sequence into which DNA can be inserted to be cloned. The vector can replicate autonomously in a host cell, and can be further characterized by one or a small number of endonuclease recognition sites at which such DNA sequences can be cut in a determinable fashion and into which DNA can be inserted. The vector can further contain a marker suitable for use in the identification of cells transformed with the vector. Markers, for example, are tetracycline resistance or ampicillin resistance. The words "cloning vehicle" are sometimes used for "vector."

Expression. Expression is the process by which a structural gene produces a polypeptide. It involves transcription of the gene into mRNA, and the translation of such mRNA into polypeptide(s).

Expression Vector. A vector or vehicle similar to a cloning vector but which is capable of expressing a gene which has been cloned into it, after transformation into a host. The cloned gene is usually placed under the control of (i.e., operably linked to) certain control sequences such as promoter sequences.

Expression control sequences will vary depending on whether the vector is designed to express the operably linked gene in a prokaryotic or eukaryotic host and can additionally contain transcriptional elements such as enhancer elements, termination sequences, tissue-specificity elements, and/or translational initiation and termination sites.

Functional Derivative. A "functional derivative" of a sequence, either protein or nucleic acid, is a molecule that possesses a biological activity (either functional or structural) that is substantially similar to a biological activity of the protein or nucleic acid sequence. A functional derivative of a protein can contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties can improve the molecule's solubility, absorption, biological half life, and the like. The moieties can alternatively decrease the toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art.

Variant. A "variant" of a protein or nucleic acid is meant to refer to a molecule substantially similar in structure and biological activity to either the protein or nucleic acid. Thus, provided that two molecules possess a common activity and can substitute for each other, they are considered variants as that term is used herein even if the composition or secondary, tertiary, or quaternary structure of one of the molecules is not identical to that found in the other, or if the amino acid or nucleotide sequence is not identical.

Allele. An "allele" is an alternative form of a gene occupying a given locus on the chromosome.

Mutation. A "mutation" is any detectable change in the genetic material which can be transmitted to daughter cells and possibly even to succeeding generations giving rise to mutant cells or mutant individuals. If the descendants of a mutant cell give rise only to somatic cells in multicellular organisms, a mutant spot or area of cells arises. Mutations in the germ line of sexually reproducing organisms can be transmitted by the gametes to the next generation resulting in an individual with the new mutant condition in both its somatic and germ cells. A mutation can be any (or a combination of) detectable, unnatural change affecting the chemical or physical constitution, mutability, replication, phenotypic function, or recombination of one or more deoxyribonucleotides; nucleotides can be added, deleted, substituted for, inverted, or transposed to new positions with and without inversion. Mutations can occur spontaneously and can be induced experimentally by application of mutagens. A mutant variation of a nucleic acid molecule results from a mutation. A mutant polypeptide can result from a mutant nucleic acid molecule.

Species. A "species" is a group of actually or potentially interbreeding natural populations. A species variation within a nucleic acid molecule or protein is a change in the nucleic acid or amino acid sequence that occurs among species and can be determined by DNA sequencing of the molecule in question.

Polyacrylamide Gel Electrophoresis (PAGE). The most commonly used technique (though not the only one) for achieving a fractionation of polypeptides on the basis of size is polyacrylamide gel electrophoresis. The principle of this method is that polypeptide molecules migrate through the gel as though it were a sieve that retards the movement of the largest molecules to the greatest extent and the movement of the smallest molecules to the least extent. Note that the smaller the polypeptide fragment, the greater the mobility under electrophoresis in the polyacrylamide gel. Both before and during electrophoresis, the polypeptides typically are continuously exposed to the detergent sodium dodecyl sulfate (SDS), under which conditions the polypeptides are denatured. Native gels are run in the absence of SDS. The polypeptides fractionated by polyacrylamide gel electrophoresis can be visualized directly by a staining procedure if the number of polypeptide components is small.

Western Transfer Procedure. The purpose of the Western transfer procedure (also referred to as blotting) is to physically transfer polypeptides fractionated by polyacrylamide gel electrophoresis onto a nitrocellulose filter paper or another appropriate surface or method, while retaining the relative positions of polypeptides resulting from the fractionation procedure. The blot is then probed with an antibody that specifically binds to the polypeptide of interest.

Purified. A "purified" protein or nucleic acid is a protein or nucleic acid that has been separated from a cellular component. "Purified" proteins or nucleic acids have been purified to a level of purity not found in nature.

Substantially Pure. A "substantially pure" protein or nucleic acid is a protein or nucleic acid preparation that is lacking in all other cellular components.

BRIEF DESCRIPTION OF THE DRAWINGS

Having thus generally described the invention, reference will now be made to the accompanying drawings, showing by way of illustration a preferred embodiment thereof, and in which:

FIG. 3 is a schematic representation comparing cDNA clones pMB9 and λDD3.6.

FIG. 5A-F (A) a PCA3 cDNA structure; (B)-(F) a PCA3 nucleotide and amino acid cDNA sequence (SEQ ID NOs:6 and 7); putative poly-adenylation signals are underlined.

Figure 1:
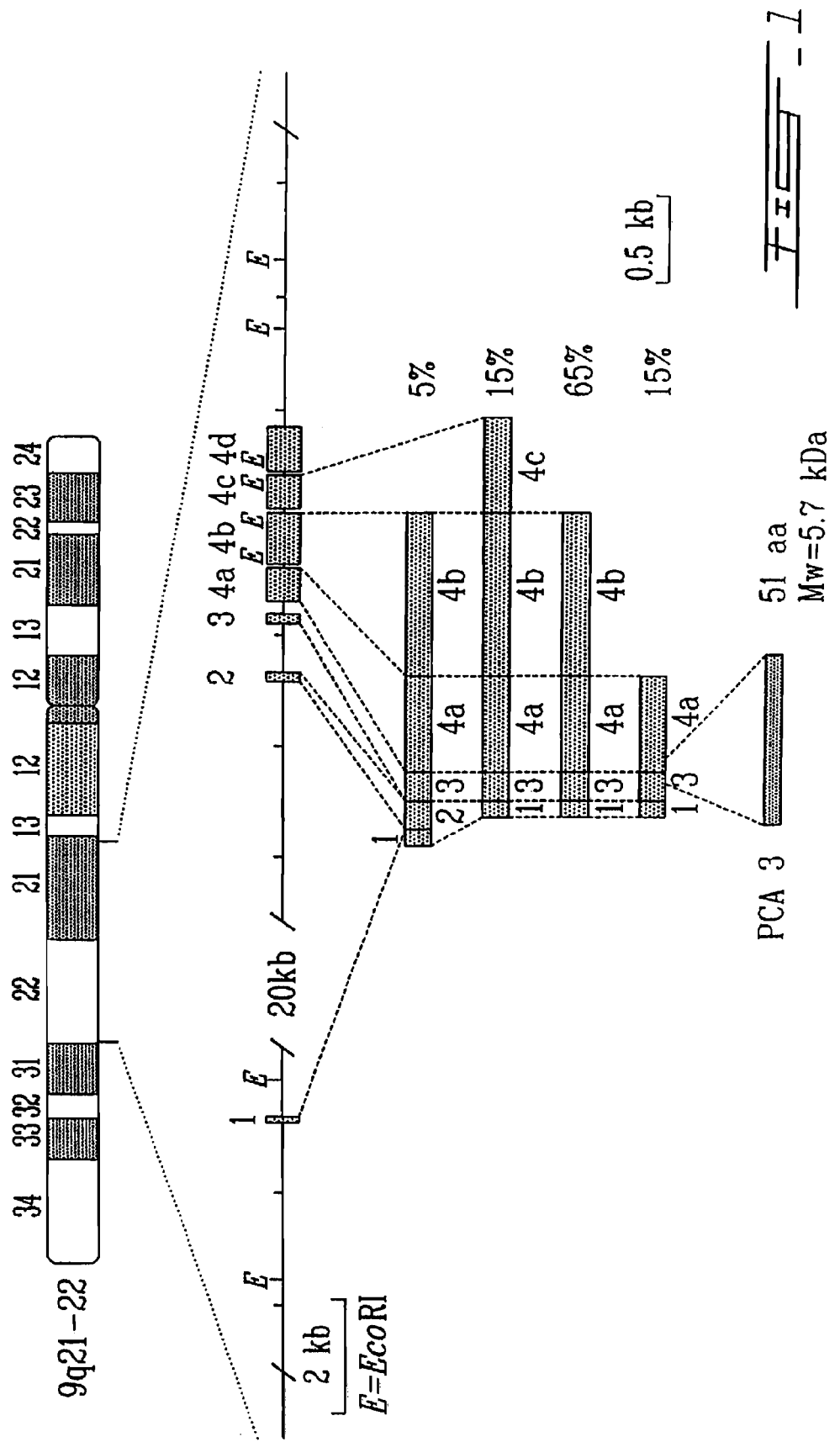
FIG. 1 shows the genomic structure of the PCA3 gene.

Other objects, advantages and features of the present invention will become more apparent upon reading of the following non-restrictive description of preferred embodiments with reference to the accompanying drawings which are exemplary and should not be interpreted as limiting the scope of the present invention.

DESCRIPTION OF ILLUSTRATIVE EMBODIMENTS

For purposes of clarity of disclosure, and not by way of limitation, the detailed description of the invention is divided into the following subsections:

I. Isolated Nucleic Acid Molecules Coding for PCA3 Polypeptides.

II. Purified PCA3 Polypeptides.

III. A Nucleic Acid for the Specific Detection of PCA3 Nucleic Acid.

IV. A Method of Detecting the Presence of PCA3 Nucleic Acid in a Sample.

V. A Kit for Detecting the Presence of PCA3 Nucleic Acid in a Sample.

VI. DNA Constructs Comprising a PCA3 Nucleic Acid Molecule and Cells Containing These Constructs.

VII. An Antibody Having Binding Affinity to a PCA3 Polypeptide and a Hybridoma Containing the Antibody.

VIII. A Method of Detecting a PCA3 Polypeptide or Antibody in a Sample.

IX. A Diagnostic Kit Comprising a PCA3 Protein or Antibody.

X. Diagnostic Screening.

XI. Therapeutic Treatments.

XII. Transgenic PCA3 Non-human Animals.

I. Isolated Nucleic Acid Molecules Coding for PCA3 Polypeptides

In one embodiment, the present invention relates to isolated (purified) PCA3 nucleic acid molecules. Preferably, the PCA3 nucleic acid molecule comprises a polynucleotide sequence at least 90% identical (more preferably, 95%, 96%, 97%, 98%, 99% or 100% identical) to a sequence selected from the group consisting of:

(a) a nucleotide sequence encoding a PCA3 polypeptide comprising the complete amino acid sequence in SEQ ID NO:2 or SEQ ID NO:7;

(b) a nucleotide sequence encoding a PCA3 polypeptide comprising the complete amino acid sequence encoded by the polynucleotide clone contained in the deposit at the Centraal voor Schimmelcultures as accession number CBS 682.97;

(c) a nucleotide sequence encoding a PCA3 polypeptide comprising the complete amino acid sequence encoded by the polynucleotide clone contained in the deposit at the Centraal voor Schimmelcultures as accession number CBS 100521; and (d) a nucleotide sequence complementary to any of the nucleotide sequences in (a), (b), or (c).

pMB9 is a PCA3 cDNA clone which contains exons 1, 2, 3, 4a and 4b of the PCA3 gene. pMB9 was deposited at the Phabagen Collection, University of Utrecht, Padualaan 8, 3584 CH Utrecht (which is a division of the Centraalbureau voor Schimmelcultures, Oosterstratt1, Postbus 273, 3740 AG Baarn) under the regulations of the Budapest Treaty on Apr. 10, 1997 as accession number CBS 682.97.

λDD3.6 is a PCA3 cDNA clone which contains exons 3, 4a, 4b, 4c, and 4d. λDD3.6 was deposited at the Phabagen Collection, University of Utrecht, Padualaan 8, 3584 CH Utrecht (which is a division of the Centraalbureau voor Schimmelcultures, Oosterstratt1, Postbus 273, 3740 AG Baarn) under the regulations of the Budapest Treaty on Mar. 27, 1998 as accession number CBS 100521.

In one preferred embodiment, the isolated nucleic acid molecule comprises a PCA3 nucleotide sequence with greater than 90% identity or similarity to the nucleotide sequence present in SEQ ID NO:1 (preferably greater than 95%, 96%, 97%, 98%, 99% or 100%). In another preferred embodiment, the isolated nucleic acid molecule comprises the PCA3 coding sequence present in SEQ ID NO:1. In another embodiment, the isolated nucleic acid molecule encodes the PCA3 amino acid sequence present in SEQ ID NO:2 or SEQ ID NO:7. In yet another embodiment, the isolated nucleic acid molecule comprises a PCA3 nucleotide sequence with greater than 90% identity or similarity to the nucleotide sequence present in SEQ ID NO:6 (preferably greater than 95%, 96%, 97%, 98%, 99% or 100%). In another preferred embodiment, the isolated nucleic acid molecule comprises the PCA3 coding sequence present in SEQ ID NO:6.

Also included within the scope of this invention are isolated nucleic acids comprising cDNA splice variants of PCA3 or polynucleotide sequences which are at least 90% identical thereto, preferably at least 95% identical thereto. In view of the fact that virtually all combinations of exons are possible, non-limiting examples of such splice variants include isolated PCA3 nucleic acids comprising exons 1, 2, 3, 4a and 4b (SEQ ID NO:1); exons 1, 3, 4a, 4b, and 4c (SEQ ID NO:3 and region 4c which is contiguous to region 4b, see FIG. 1); exons 1, 3, 4a, 4b, 4c, and 4d (SEQ ID NO:3 and region 4c which is contiguous to region 4b and region 4d which is contiguous to region 4c, see FIG. 1); exons 1, 3, 4a, and 4b (SEQ ID NO:3); exons 1, 3, and 4a (SEQ ID NO:4); exons 1, 2, 3, 4a, 4b, 4c, and 4d (SEQ ID NO:6) Preferably, the PCA3 nucleic acid molecule comprises a polynucleotide sequence at least 90% identical (more preferably, 95%, 96%, 97%, 98%, 99% or 100% identical) to one of the above-described splice variants.

Also included within the scope of this invention are the functional equivalents of the herein-described isolated nucleic acid molecules and derivatives thereof. For example, the nucleic acid sequences depicted in SEQ ID NO:1 or SEQ ID NO:6 can be altered by substitutions, additions or deletions that provide for functionally equivalent molecules. Due to the degeneracy of nucleotide coding sequences, other DNA sequences which encode substantially the same amino acid sequence as depicted in SEQ ID NO:2 and SEQ ID NO:7 can be used in the practice of the present invention. These include but are not limited to nucleotide sequences comprising all or portions of PCA3 nucleic acid depicted in SEQ ID NO:1, 3, 4 or 6, which are altered by the substitution of different codons that encode a functionally equivalent amino acid residue within the sequence.

In addition, the nucleic acid sequence can comprise a nucleotide sequence which results from the addition, deletion or substitution of at least one nucleotide to the 5'-end and/or the 3'-end of the nucleic acid formula shown in SEQ ID NO:1, 3, 4, or 6 or a derivative thereof. Any nucleotide or polynucleotide can be used in this regard, provided that its addition, deletion or substitution does not substantially alter the amino acid sequence of SEQ ID NO:2, or SEQ ID NO:7 which is encoded by the nucleotide sequence. Moreover, the nucleic acid molecule of the present invention can, as necessary, have restriction endonuclease recognition sites added to its 5'-end and/or 3'-end. All variations of the nucleotide sequence of the PCA3 nucleotide coding sequence and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

A. Isolation of Nucleic Acid

In one aspect of the present invention, isolated nucleic acid molecules coding for polypeptides having amino acid sequences corresponding to PCA3 are provided. In particular, the nucleic acid molecule can be isolated from a biological sample containing PCA3 RNA or DNA.

The nucleic acid molecule can be isolated from a biological sample containing PCA3 RNA using the techniques of cDNA cloning and subtractive hybridization. The nucleic acid molecule can also be isolated from a cDNA library using a homologous probe.

The nucleic acid molecule can be isolated from a biological sample containing genomic DNA or from a genomic library. Suitable biological samples include, but are not limited to, whole organisms, organs, tissues, blood and cells. The method of obtaining the biological sample will vary depending upon the nature of the sample.

One skilled in the art will realize that genomes can be subject to slight allelic variations between individuals. Therefore, the isolated nucleic acid molecule is also intended to include allelic variations, so long as the sequence is a functional derivative of the PCA3 coding sequence. When a PCA3 allele does not encode the identical sequence to that found in SEQ ID NO:1 or 6, it can be isolated and identified as PCA3 using the same techniques used herein, and especially PCR techniques to amplify the appropriate gene with primers based on the sequences disclosed herein.

One skilled in the art will realize that organisms other than humans will also contain PCA3 genes (for example, eukaryotes; more specifically, mammals, birds, fish, and plants; more specifically, gorillas, rhesus monkeys, and chimpanzees). The invention is intended to include, but not be limited to, PCA3 nucleic acid molecules isolated from the above-described organisms.

B. Synthesis of Nucleic Acid

Isolated nucleic acid molecules of the present invention are also meant to include those chemically synthesized. For example, a nucleic acid molecule with the nucleotide sequence which codes for the expression product of a PCA3 gene can be designed and, if necessary, divided into appropriate smaller fragments. Then an oligomer which corresponds to the nucleic acid molecule, or to each of the divided fragments, can be synthesized. Such synthetic oligonucleotides can be prepared, for example, by the triester method of Matteucci et al., *J. Am. Chem. Soc.* 103:3185-3191 (1981) or by using an automated DNA synthesizer.

An oligonucleotide can be derived synthetically or by cloning. If necessary, the 5'-ends of the oligomers can be phosphorylated using T4 polynucleotide kinase. Kinasing of single strands prior to annealing or for labeling can be achieved using an excess of the enzyme. If kinasing is for the labeling of probe, the ATP can contain high specific activity radioisotopes. Then, the DNA oligomer can be subjected to annealing and ligation with T4 ligase or the like.

II. Purified PCA3 Polypeptides

In another embodiment, the present invention relates to a purified polypeptide (preferably, substantially pure) having an amino acid sequence corresponding to PCA3, or a functional derivative thereof. In a preferred embodiment, the polypeptide has the amino acid sequence set forth in SEQ ID NO:2 or 7 or mutant or species variation thereof, or at least 80% identity or at least 90% similarity thereof (preferably, at least 90%, 95%, 96%, 97%, 98%, or 99% identity or at least 95%, 96%, 97%, 98%, or 99% similarity thereof), or at least 6 contiguous amino acids thereof (preferably, at least 10, 15, 20, 25, or 50 contiguous amino acids thereof).

In a preferred embodiment, the invention relates to PCA3 epitopes. The epitope of these polypeptides is an immunogenic or antigenic epitope. An immunogenic epitope is that part of the protein which elicits an antibody response when the whole protein is the immunogen. An antigenic epitope is a fragment of the protein which can elicit an antibody response. Methods of selecting antigenic epitope fragments are well known in the art. See, Sutcliffe et al., *Science* 219: 660-666 (1983). Antigenic epitope-bearing peptides and polypeptides of the invention are useful to raise an immune response that specifically recognizes the polypeptides. Antigenic epitope-bearing peptides and polypeptides of the invention comprise at least 7 amino acids (preferably, 9, 10, 12, 15 or 20 amino acids) of the proteins of the invention. An example of a antigenic peptide is HTQEAQKEAQR (SEQ ID NO:5).

Amino acid sequence variants of PCA3 can be prepared by mutations in the DNA. Such variants include, for example, deletions from, or insertions or substitutions of, residues within the amino acid sequence shown in SEQ ID NO:2 or 7. Any combination of deletion, insertion, and substitution can also be made to arrive at the final construct, provided that the final construct possesses the desired activity.

While the site for introducing an amino acid sequence variation is predetermined, the mutation per se need not be predetermined. For example, to optimize the performance of a mutation at a given site, random mutagenesis can be conducted at the target codon or region and the expressed PCA3 variants screened for the optimal combination of desired activity. Techniques for making substitution mutations at predetermined sites in DNA having a known sequence are well known, for example, site-specific mutagenesis.

Preparation of a PCA3 variant in accordance herewith is preferably achieved by site-specific mutagenesis of DNA that encodes an earlier prepared variant or a nonvariant version of the protein. Site-specific mutagenesis allows the production of PCA3 variants through the use of specific oligonucleotide sequences that encode the DNA sequence of the desired mutation. In general, the technique of site-specific mutagenesis is well known in the art, as exemplified by publications such as Adelman et al., *DNA* 2:183 (1983) and Ausubel et al. "Current Protocols in Molecular Biology", J. Wiley & Sons, NY, N.Y., 1996.

Amino acid sequence deletions generally range from about 1 to 30 residues, more preferably 1 to 10 residues, and typically are contiguous.

Amino acid sequence insertions include amino and/or carboxyl-terminal fusions of from one residue to polypeptides of essentially unrestricted length, as well as intrasequence insertions of single or multiple amino acid residues. Intrasequence insertions (i.e., insertions within the complete PCA3 sequence) can range generally from about 1 to 10 residues, more preferably 1 to 5.

The third group of variants are those in which at least one amino acid residue in the PCA3 molecule, and preferably, only one, has been removed and a different residue inserted in its place. Such substitutions preferably are made in accordance with the following Table 1 when it is desired to modulate finely the characteristics of PCA3.

TABLE 1

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |

TABLE 1-continued

| Original Residue | Exemplary Substitutions |
|---|---|
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Some deletions and insertions, and substitutions are not expected to produce radical changes in the characteristics of PCA3. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native PCA3 encoding-nucleic acid, expression of the variant nucleic acid in recombinant cell culture, and, optionally, purification from the cell culture, for example, by immunoaffinity adsorption on a column (to absorb the variant by binding it to at least one remaining immune epitope). The activity of the cell lysate or purified PCA3 molecule variant is then screened in a suitable screening assay for the desired characteristic. For example, a change in the immunological character of the PCA3 molecule, such as affinity for a given antibody, is measured by a competitive type immunoassay. Changes in immunomodulation activity are measured by the appropriate assay. Modifications of such protein properties as redox or thermal stability, hydrophobicity, susceptibility to proteolytic degradation or the tendency to aggregate with carriers or into multimers are assayed by methods well known to the ordinarily skilled artisan.

A variety of methodologies known in the art can be utilized to obtain the peptide of the present invention. In one embodiment, the peptide is purified from tissues or cells which naturally produce the peptide. Alternatively, the above-described isolated nucleic acid fragments can be used to express the PCA3 protein in any organism. The samples of the present invention include cells, protein extracts or membrane extracts of cells, or biological fluids. The sample will vary based on the assay format, the detection method and the nature of the tissues, cells or extracts used as the sample.

Any organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: immunochromotography, size-exclusion chromatography, HPLC, ion-exchange chromatography, and immuno-affinity chromatography.

In a preferred embodiment, the purification procedures comprise ion-exchange chromatography and size exclusion chromatography. Any one of a large number of ion-exchange resins known in the art can be employed, including for example, monoQ, sepharose Q, macro-prepQ, AG1-X2, or HQ. Examples of suitable size exclusion resins include, but are not limited to, Superdex 200, Superose 12, and Sephycryl 200. Elution can be achieved with aqueous solutions of potassium chloride or sodium chloride at concentrations ranging from 0.01M to 2.0M.

III. A Nucleic Acid for the Specific Detection of PCA3 Nucleic Acid

In another embodiment, the present invention relates to a nucleic acid for the specific detection of the presence of PCA3 nucleic acid in a sample comprising the above-described nucleic acid molecules or at least a fragment thereof which binds under stringent conditions to PCA3 nucleic acid.

In one preferred embodiment, the present invention relates to an isolated nucleic acid consisting of 10 to 1000 nucleotides (preferably, 10 to 500, 10 to 100, 10 to 50, 10 to 35, 20 to 1000, 20 to 500, 20 to 100, 20 to 50, or 20 to 35) which hybridizes preferentially to RNA or DNA encoding PCA3 or to a PCA3 gene but not to RNA or DNA of which is not related to PCA3, wherein said nucleic acid probe is or is complementary to a nucleotide sequence consisting of at least 10 consecutive nucleotides (preferably, 15, 18, 20, 25, or 30) from the nucleic acid molecule comprising a polynucleotide sequence at least 90% identical to a sequence selected from the group consisting of:

(a) a nucleotide sequence encoding the PCA3 polypeptide comprising the complete amino acid sequence in SEQ ID NO:2 or 7;

(b) a nucleotide sequence encoding the PCA3 polypeptide comprising the complete amino acid sequence encoded by the polynucleotide clone contained in the deposit at the Centraal voor Schimmelcultures as accession number CBS 682.97, respectively;

(c) a nucleotide sequence encoding the PCA3 polypeptide comprising the complete amino acid sequence encoded by the polynucleotide clone contained in the deposit at the Centraal voor Schimmelcultures as accession number CBS 100521, respectively;

(d) a nucleotide sequence encoding the PCA3 gene comprising the nucleotide sequence in SEQ ID NO:1, 3, 4, or 6;

(e) a nucleotide sequence encoding an exon of the PCA3 gene comprising nucleotides 1-98, 99-263, 264-446, 447-985 or 986-2037 as set forth in SEQ ID NO:1;

(f) a nucleotide sequence encoding an exon of the PCA3 gene comprising nucleotides 1-120, 121-285, 286-468, 469-1007, 1008-2066, 2067-2622 or 2623-3582 as set forth in SEQ ID NO:6;

(g) a nucleotide sequence complementary to any of the nucleotide sequences in (a), (b), (c), (d), (e) or (f); and (h) a nucleotide sequence as previously described above.

Preferably, the nucleic acid does not specifically hybridize to nucleotides 511-985 of SEQ ID NO:1, to nucleotides 567-961 of SEQ ID NO:1, to nucleotides 533-1007 of SEQ ID NO:6, or to nucleotides 589-983 of SEQ ID NO:6.

Complementary sequences are also known as antisense nucleic acids when they comprise sequences which are complementary to the coding strand.

Examples of specific nucleic acid probes which can be used in the present invention are set forth in Table 2, below.

TABLE 2

NUCLEIC ACID PROBES

|  | Size (no. of bases) | Nucleotides |
|---|---|---|
| Exon 1 | 98 | 1-98 of SEQ ID NO: 1 |
| Exon 2 | 165 | 99-263 of SEQ ID NO: 1 |
| Exon 3 | 183 | 264-446 of SEQ ID NO: 1 |
| Exon 4a | 539 | 447-985 of SEQ ID NO: 1 |
| Exon 4b | 1052 | 986-2037 of SEQ ID NO: 1 |
| Probe 1 | 20 | 1-20 of SEQ ID NO: 1 |
| Probe 2 | 30 | 1-30 of SEQ ID NO: 1 |
| Probe 3 | 40 | 1-40 of SEQ ID NO: 1 |
| Probe 4 | 20 | 381-400 of SEQ ID NO: 1 |
| Probe 5 | 30 | 381-410 of SEQ ID NO: 1 |
| Probe 6 | 20 | 401-420 of SEQ ID NO: 1 |
| Probe 7 | 30 | 401-430 of SEQ ID NO: 1 |
| Probe 8 | 20 | 511-530 of SEQ ID NO: 1 |
| Probe 9 | 30 | 501-530 of SEQ ID NO: 1 |
| Probe 10 | 20 | 77-98 of SEQ ID NO: 1 |
| Probe 11 | 20 | 99-118 of SEQ ID NO: 1 |
| Probe 12 | 20 | 244-263 of SEQ ID NO: 1 |
| Probe 13 | 20 | 264-283 of SEQ ID NO: 1 |
| Probe 14 | 20 | 427-446 of SEQ ID NO: 1 |
| Probe 15 | 20 | 447-466 of SEQ ID NO: 1 |
| Exon 1 | 120 | 1-120 of SEQ ID NO: 6 |
| Exon 2 | 165 | 121-285 of SEQ ID NO: 6 |
| Exon 3 | 183 | 286-468 of SEQ ID NO: 6 |
| Exon 4a | 539 | 469-1007 of SEQ ID NO: 6 |
| Exon 4b | 1059 | 1008-2066 of SEQ ID NO: 6 |
| Exon 4c | 556 | 2067-2622 of SEQ ID NO: 6 |
| Exon 4d | 960 | 2623-3582 of SEQ ID NO: 6 |

Of course, as will be understood by the person of ordinary skill, a multitude of additional probes can be designed from the same or other region of SEQ ID NO:1 as well as from SEQ ID NO:6 and other sequences of the present invention.

The nucleic acid probe can be used to probe an appropriate chromosomal or cDNA library by usual hybridization methods to obtain another nucleic acid molecule of the present invention. A chromosomal DNA or cDNA library can be prepared from appropriate cells according to recognized methods in the art (cf. *Molecular Cloning: A Laboratory Manual*, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the PCA3 amino acid sequence. Thus, the synthesized nucleic acid probes can be used as primers in a polymerase chain reaction (PCR) carried out in accordance with recognized PCR techniques, essentially according to *PCR Protocols, A Guide to Methods and Applications*, edited by Michael et al., Academic Press, 1990, utilizing the appropriate chromosomal, cDNA or cell line library to obtain the fragment of the present invention.

One skilled in the art can readily design such probes based on the sequence disclosed herein using methods of computer alignment and sequence analysis known in the art (cf. *Molecular Cloning: A Laboratory Manual, second edition*, edited by Sambrook, Fritsch, & Maniatis, Cold Spring Harbor Laboratory, 1989).

The hybridization probes of the present invention can be labeled by standard labeling techniques such as with a radiolabel, enzyme label, fluorescent label, biotin-avidin label, chemiluminescence, and the like. After hybridization, the probes can be visualized using known methods.

The nucleic acid probes of the present invention include RNA, as well as DNA probes, such probes being generated using techniques known in the art.

In one embodiment of the above described method, a nucleic acid probe is immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

IV. A Method of Detecting the Presence of PCA3 Nucleic Acid in a Sample

In another embodiment, the present invention relates to a method of detecting the presence of PCA3 nucleic acid in a sample comprising a) contacting the sample with the above-described nucleic acid probe, under specific hybridization conditions such that hybridization occurs, and b) detecting the presence of the probe bound to the nucleic acid molecule. One skilled in the art would select the nucleic acid probe according to techniques known in the art as described above. Samples to be tested include but should not be limited to RNA or DNA samples from human tissue.

V. A Kit for Detecting the Presence of PCA3 Nucleic Acid in a Sample

In another embodiment, the present invention relates to a kit for detecting the presence of PCA3 nucleic acid in a sample comprising at least one container means having disposed therein the above-described nucleic acid probe. In a preferred embodiment, the kit further comprises other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like.

One skilled in the art will readily recognize that the nucleic acid probes described in the present invention can readily be incorporated into one of the established kit formats which are well known in the art.

VI. DNA Constructs Comprising a PCA3 Nucleic Acid Molecule and Cells Containing these Constructs In another embodiment, the present invention relates to a recombinant DNA molecule comprising, 5' to 3', a promoter effective to initiate transcription in a host cell and the above-described nucleic acid molecules. In another embodiment, the present invention relates to a recombinant DNA molecule comprising a vector and an above-described nucleic acid molecule.

In another embodiment, the present invention relates to a nucleic acid molecule comprising a transcriptional control region functional in a cell, a sequence complimentary to an RNA sequence encoding an amino acid sequence corresponding to the above-described polypeptide, and a transcriptional termination region functional in the cell.

Preferably, the above-described molecules are isolated and/or purified DNA molecules.

In another embodiment, the present invention relates to a cell or non-human organism that contains an above-described nucleic acid molecule.

In another embodiment, the peptide is purified from cells which have been altered to express the peptide.

As used herein, a cell is said to be "altered to express a desired peptide" when the cell, through genetic manipulation, is made to produce a protein which it normally does not produce or which the cell normally produces at low levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression can vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the PCA3 coding sequence can be obtained by the above-described methods. This region can be retained for its transcriptional termination regulatory sequences, such as termination and polyadenylation. Thus, by retaining the 3'-region naturally contiguous to the DNA sequence encoding a PCA3 gene, the transcriptional termination signals can be provided. Where the transcriptional termination signals are not satisfactorily functional in the expression host cell, then a 3' region functional in the host cell can be substituted.

Two DNA sequences (such as a promoter region sequence and a PCA3 coding sequence) are said to be operably linked if the nature of the linkage between the two DNA sequences does not (1) result in the introduction of a frame-shift mutation, (2) interfere with the ability of the promoter region sequence to direct the transcription of a PCA3 coding sequence, or (3) interfere with the ability of the PCA3 coding sequence to be transcribed by the promoter region sequence. Thus, a promoter region would be operably linked to a DNA sequence if the promoter were capable of effecting transcription of that DNA sequence.

The present invention encompasses the expression of the PCA3 coding sequence (or a functional derivative thereof) in either prokaryotic or eukaryotic cells. Prokaryotic hosts are, generally, the most efficient and convenient for the production of recombinant proteins and, therefore, are preferred for the expression of the PCA3 coding sequence.

Prokaryotes most frequently are represented by various strains of *E. coli*. However, other microbial strains can also be used, including other bacterial strains. In prokaryotic systems, plasmid vectors that contain replication sites and control sequences derived from a species compatible with the host can be used. Examples of suitable plasmid vectors include pBR322, pUC18, pUC19, pUC118, pUC119 and the like; suitable phage or bacteriophage vectors include λgt10, λgt11 and the like; and suitable virus vectors include pMAM-neo, pKRC and the like. Preferably, the selected vector of the present invention has the capacity to replicate in the selected host cell.

Recognized prokaryotic hosts include bacteria such as *E. coli, Bacillus, Streptomyces, Pseudomonas, Salmonella, Serratia*, and the like. However, under such conditions, the peptide will not be glycosylated. The prokaryotic host must be compatible with the replicon and control sequences in the expression plasmid.

To express PCA3 in a prokaryotic cell, it is necessary to operably link the PCA3 coding sequence to a functional prokaryotic promoter. Such promoters can be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pBR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176-182 (1985)) and the ζ-28-specific promoters of *B. subtilis* (Gilman et al., *Gene sequence* 32:11-20 (1984)), the promoters of the bacteriophages of *Bacillus* (Gryczan, In: *The Molecular Biology of the Bacilli*, Academic Press, Inc., NY (1982)), and *Streptomyces* promoters (Ward et al., *Mol. Gen. Genet.* 203:468-478 (1986)). Prokaryotic promoters are reviewed by Glick (*J. Ind. Microbiol.* 1:277-282 (1987)); Cenatiempo (*Biochimie* 68:505-516 (1986)); and Gottesman (*Ann. Rev. Genet.* 18:415-442 (1984)).

Proper expression in a prokaryotic cell also requires the presence of a ribosome binding site upstream of the gene sequence-encoding sequence. Such ribosome binding sites are disclosed, for example, by Gold et al. (*Ann. Rev. Microbiol.* 35:365-404 (1981)).

The selection of control sequences, expression vectors, transformation methods, and the like, are dependent on the type of host cell used to express the gene. As used herein, "cell", "cell line", and "cell culture" can be used interchangeably and all such designations include progeny. Thus, the words "transformants" or "transformed cells" include the primary subject cell and cultures derived therefrom, without regard to the number of transfers. It is also understood that all progeny can not be precisely identical in DNA content, due to deliberate or inadvertent mutations. However, as defined, mutant progeny have the same functionality as that of the originally transformed cell.

Host cells which can be used in the expression systems of the present invention are not strictly limited, provided that they are suitable for use in the expression of the PCA3 peptide of interest. Suitable hosts include eukaryotic cells.

Preferred eukaryotic hosts include, for example, yeast, fungi, insect cells, mammalian cells either in vivo, or in tissue culture. Preferred mammalian cells include HeLa cells, cells of fibroblast origin such as VERO or CHO-K1, or cells of lymphoid origin and their derivatives.

In addition, plant cells are also available as hosts, and control sequences compatible with plant cells are available, such as the cauliflower mosaic virus 3S and 19S, and nopaline synthase promoter and polyadenylation signal sequences.

Another preferred host is an insect cell, for example *Drosophila* larvae. Using insect cells as hosts, the *Drosophila* alcohol dehydrogenase promoter can be used, Rubin, *Science* 240:1453-1459 (1988). Alternatively, baculovirus vectors can be engineered to express large amounts of PCA3 in insect cells (Jasny, *Science* 238:1653 (1987); Miller et al., In: *Genetic Engineering* (1986), Setlow, J. K., et al., eds., *Plenum*, Vol. 8, pp. 277-297).

Different host cells have characteristic and specific mechanisms for the translational and post-translational processing and modification (e.g., glycosylation, cleavage) of proteins. Appropriate cell lines or host systems can be chosen to ensure the desired modification and processing of the foreign protein expressed.

Any of a series of yeast gene sequence expression systems can be utilized which incorporate promoter and termination elements from the actively expressed gene sequences coding for glycolytic enzymes. These enzymes are produced in large quantities when yeast are grown in mediums rich in glucose. Known glycolytic gene sequences can also provide very efficient transcriptional control signals.

Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of PCA3.

A wide variety of transcriptional and translational regulatory sequences can be employed, depending upon the nature of the host. The transcriptional and translational regulatory signals can be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, can be employed. Transcriptional initiation regulatory signals can be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

As discussed above, expression of PCA3 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273-288 (1982)); the TK promoter of Herpes virus (McKnight, *Cell* 31:355-365 (1982)); the SV40 early promoter (Benoist et al., *Nature (London)* 290:304-310 (1981)); the yeast gal4 gene sequence promoter (Johnston et al., *Proc. Natl. Acad. Sci. (USA)* 79:6971-6975 (1982); Silver et al., *Proc. Natl. Acad. Sci. (USA)* 81:5951-5955 (1984)) and the CMV immediate-early gene promoter (Thomsen et al., *Proc. Natl. Acad. Sci. (USA)* 81:659-663 (1984).

As is widely known, translation of eukaryotic mRNA is initiated at the codon which encodes the first methionine. For this reason, it is preferable to ensure that the linkage between a eukaryotic promoter and a PCA3 coding sequence does not contain any intervening codons which are capable of encoding a methionine (i.e., AUG). The presence of such codons results either in a formation of a fusion protein (if the AUG codon is in the same reading frame as the PCA3 coding sequence) or a frame-shift mutation (if the AUG codon is not in the same reading frame as the PCA3 coding sequence).

A PCA3 nucleic acid molecule and an operably linked promoter can be introduced into a recipient prokaryotic or eukaryotic cell either as a non-replicating DNA (or RNA) molecule, which can either be a linear molecule or, more preferably, a closed covalent circular molecule. Since such molecules are incapable of autonomous replication, the expression of the gene can occur through the transient expression of the introduced sequence. Alternatively, permanent expression can occur through the integration of the introduced DNA sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker can provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements can also be needed for optimal synthesis of single chain binding protein mRNA. These elements can include splice signals, as well as transcription promoters, enhancer signal sequences, and termination signals. cDNA expression vectors incorporating such elements include those described by Okayama, *Molec. Cell. Biol.* 3:280 (1983).

In a preferred embodiment, the introduced nucleic acid molecule will be incorporated into a plasmid or viral vector capable of autonomous replication in the recipient host. Any of a wide variety of vectors can be employed for this purpose. Factors of importance in selecting a particular plasmid or viral vector include: the ease with which recipient cells that contain the vector can be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, πVX. Such plasmids are, for example, disclosed by Sambrook (cf. *Molecular Cloning: A Laboratory Manual*, second edition, edited by Sambrook, Fritsch, & Maniatis, Cold Spring Harbor Laboratory, 1989). *Bacillus* plasmids include pC194, pC221, pT127, and the like. Such plasmids are disclosed by Gryczan (In: *The Molecular Biology of the Bacilli*, Academic Press, NY (1982), pp. 307-329). Suitable *Streptomyces* plasmids include plJ101 (Kendall et al., *J. Bacteriol.* 169:4177-4183 (1987)), and *streptomyces* bacteriophages such as ϕC31 (Chater et al., In: *Sixth International Symposium on Actinomycetales Biology*, Akademiai Kaido, Budapest, Hungary (1986), pp. 45-54). *Pseudomonas* plasmids are reviewed by John et al. (*Rev. Infect. Dis.* 8:693-704 (1986)), and Izaki (*Jpn. J. Bacteriol.* 33:729-742 (1978)).

Preferred eukaryotic plasmids include, for example, BPV, vaccinia, SV40, 2-micron circle, and the like, or their derivatives. Such plasmids are well known in the art (Botstein et al., *Miami Wntr. Symp.* 19:265-274 (1982); Broach, In: *The Molecular Biology of the Yeast Saccharomyces: Life Cycle and Inheritance*, Cold Spring Harbor Laboratory, Cold Spring Harbor, N.Y., p. 445-470 (1981); Broach, *Cell* 28:203-204 (1982); Bollon et al., *J. Clin. Hematol. Oncol.* 10:39-48 (1980); Maniatis, In: *Cell Biology: A Comprehensive Treatise*, Vol. 3, Gene Sequence Expression, Academic Press, NY, pp. 563-608 (1980)).

Once the vector or nucleic acid molecule containing the construct(s) has been prepared for expression, the DNA construct(s) can be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of PCA3. This can take place in the transformed cells as such, or following the induction of these cells to differentiate (for example, by administration of bromodeoxyuracil to neuroblastoma cells or the like).

VII. An Antibody Having Binding Affinity to a PCA3 Polypeptide and a Hybridoma Containing the Antibody In another embodiment, the present invention relates to an antibody having binding affinity specifically to a PCA3 polypeptide as described above or specifically to a PCA3 polypeptide binding fragment thereof. An antibody binds specifically to a PCA3 polypeptide or binding fragment thereof if it does not bind to non-PCA3 polypeptides. Those which bind selectively to PCA3 would be chosen for use in methods which could include, but should not be limited to, the analysis of altered PCA3 expression in tissue containing PCA3.

The PCA3 proteins of the present invention can be used in a variety of procedures and methods, such as for the generation of antibodies, for use in identifying pharmaceutical compositions, and for studying DNA/protein interaction.

The PCA3 peptide of the present invention can be used to produce antibodies or hybridomas. One skilled in the art will recognize that if an antibody is desired, such a peptide would be generated as described herein and used as an immunogen.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the $F(ab')_2$ fragment; the Fab' fragments, Fab fragments, and Fv fragments.

Of special interest to the present invention are antibodies to PCA3 which are produced in humans, or are "humanized" (i.e. non-immunogenic in a human) by recombinant or other technology. Humanized antibodies can be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041-1043 (1988); Liu, A. Y. et al., *Proc. Natl. Acad. Sci. USA* 84:3439-3443 (1987); Liu, A. Y. et al., *J. Immunol.* 139:3521-3526 (1987); Sun, L. K. et al., *Proc. Natl. Acad. Sci. USA* 84:214-218 (1987); Nishimura, Y. et al., *Canc. Res.* 47:999-1005 (1987); Wood, C. R. et al., *Nature* 314:446-449 (1985)); Shaw et al., *J. Natl. Cancer Inst.* 80:1553-1559 (1988). General reviews of "humanized" chimeric antibodies are provided by Morrison, S. L. (*Science*, 229:1202-1207 (1985)) and by Oi, V. T. et al., *BioTechniques* 4:214 (1986)). Suitable "humanized" antibodies can be alternatively produced by CDR or CEA substitution (Jones, P. T. et al., *Nature* 321:552-525 (1986); Verhoeyan et al., *Science* 239:1534 (1988); Beidler, C. B. et al., *J. Immunol.* 141:4053-4060 (1988)).

In another embodiment, the present invention relates to a hybridoma which produces the above-described monoclonal antibody. A hybridoma is an immortalized cell line which is capable of secreting a specific monoclonal antibody.

In general, techniques for preparing monoclonal antibodies and hybridomas are well known in the art (Campbell, "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1-21 (1980)).

Any animal (mouse, rabbit, and the like) which is known to produce antibodies can be immunized with the selected polypeptide. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide can be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109-124 (1988)).

Hybridomas secreting the desired antibodies are cloned and the class and subclass is determined using procedures known in the art (Campbell, *Monoclonal Antibody Technology: Laboratory Techniques in Biochemistry and Molecular Biology*, supra (1984)).

For polyclonal antibodies, antibody containing antisera is isolated from the immunized animal and is screened for the presence of antibodies with the desired specificity using one of the above-described procedures.

In another embodiment of the present invention, the above-described antibodies are detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., *J. Histochem. Cytochem.*

18:315 (1970); Bayer et al., *Meth. Enzym.* 62:308 (1979); Engval et al., *Immunol.* 109:129 (1972); Goding, *J. Immunol. Meth.* 13:215 (1976)). The labeled antibodies of the present invention can be used for in vitro, in vivo, and in situ assays to identify cells or tissues which express a specific peptide.

In another embodiment of the present invention the above-described antibodies are immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "*Handbook of Experimental Immunology*" 4th Ed., Blackwell Scientific Publications, Oxford, England, Chapter 10 (1986); Jacoby et al., *Meth. Enzym.* 34 Academic Press, N.Y. (1974)). The immobilized antibodies of the present invention can be used for in vitro, in vivo, and in situ assays as well as in immunochromatography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides Antisense Peptides", In *Synthetic Peptides, A User's Guide*, W.H. Freeman, NY, pp. 289-307 (1992), and Kaspczak et al., *Biochemistry* 28:9230-8 (1989).

Anti-peptide peptides can be generated in one of two fashions. First, the anti-peptide peptides can be generated by replacing the basic amino acid residues found in the PCA3 peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

VIII. A Method of Detecting a PCA3 Polypeptide or Antibody in a Sample

In another embodiment, the present invention relates to a method of detecting a PCA3 polypeptide in a sample, comprising: a) contacting the sample with an above-described antibody (or protein), under conditions such that immunocomplexes form, and b) detecting the presence of the antibody bound to the polypeptide. In detail, the methods comprise incubating a test sample with one or more of the antibodies of the present invention and assaying whether the antibody binds to the test sample. Altered levels of PCA3 in a sample as compared to normal levels can indicate a specific disease (ex. prostate cancer).

In a further embodiment, the present invention relates to a method of detecting a PCA3 antibody in a sample, comprising: a) contacting the sample with an above-described PCA3 protein, under conditions such that immunocomplexes form, and b) detecting the presence of the protein bound to the antibody or antibody bound to the protein. In detail, the methods comprise incubating a test sample with one or more of the proteins of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, *An Introduction to Radioimmunoassay and Related Techniques*, Elsevier Science Publishers, Amsterdam, The Netherlands (1986); Bullock et al., *Techniques in Immunocytochemistry*, Academic Press, Orlando, Fla. Vol. 1 (1982), Vol. 2 (1983), Vol. 3 (1985); Tijssen, *Practice and Theory of Enzyme Immunoassays: Laboratory Techniques in Biochemistry and Molecular Biology*, Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

IX. A Diagnostic Kit Comprising PCA3 Protein or Antibody

In another embodiment of the present invention, a kit is provided which contains all the necessary reagents to carry out the previously described methods of detection.

The kit can comprise: i) a first container means containing an above-described antibody, and ii) second container means containing a conjugate comprising a binding partner of the antibody and a label.

The kit can comprise: i) a first container means containing an above-described protein, and preferably, ii) second container means containing a conjugate comprising a binding partner of the protein and a label. More specifically, a diagnostic kit comprises PCA3 protein as described above, to detect antibodies in the serum of potentially infected animals or humans.

In another preferred embodiment, the kit further comprises one or more other containers comprising one or more of the following: wash reagents and reagents capable of detecting the presence of bound antibodies. Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit can be as described above for nucleic acid probe kits.

One skilled in the art will readily recognize that the antibodies described in the present invention can readily be incorporated into one of the established kit formats which are well known in the art.

X. Diagnostic Screening

It is to be understood that although the following discussion is specifically directed to human patients, the teachings are also applicable to any animal that expresses PCA3.

The diagnostic and screening methods of the invention are especially useful for a patient suspected of being at risk for developing a disease associated with an altered expression level of PCA3 based on family history, or a patient in wt is desired to diagnose a PCA3-related disease (ex. prostate cancer).

According to the invention, presymptomatic screening of an individual in f such screening is now possible using DNA encoding the PCA3 protein or the PCA3 gene of the invention or fragments thereof. The screening method of the invention allows a presymptomatic diagnosis, including prenatal diagnosis, of the presence of a missing or aberrant PCA3 gene in individuals, and thus an opinion concerning the likelihood that such individual would develop or has developed a PCA3-associated disease. This is especially valuable for the identification of carriers of altered or missing PCA3 genes, for example, from individuals with a family history of a PCA3-associated disease. Early diagnosis is also desired to maximize appropriate timely intervention.

In one preferred embodiment of the method of screening, a tissue sample would be taken from such individual, and screened for (1) the presence of the "normal" PCA3 gene; (2) the presence of PCA3 mRNA and/or (3) the presence of PCA3 protein. The normal human gene can be characterized based upon, for example, detection of restriction digestion patterns in "normal" versus the patient's DNA, including RFLP analysis, using DNA probes prepared against the PCA3 sequence (or a functional fragment thereof) taught in the invention. Similarly, PCA3 mRNA can be characterized and compared to normal PCA3 mRNA (a) levels and/or (b) size as found in a human population not at risk of developing PCA3-associated disease using similar probes. Lastly, PCA3 protein can be (a) detected and/or (b) quantitated using a biological assay for PCA3 activity or using an immunological assay and PCA3 antibodies. When assaying PCA3 protein, the immunological assay is preferred for its speed. An (1) aberrant PCA3 DNA size pattern, and/or (2) aberrant PCA3 mRNA sizes or levels and/or (3) aberrant PCA3 protein levels would indicate that the patient is at risk for developing a PCA3-associated disease.

More specifically, a method of diagnosing the presence or predisposition to develop prostate cancer in a patient is provided herein.

The screening and diagnostic methods of the invention do not require that the entire PCA3 DNA coding sequence be used for the probe. Rather, it is only necessary to use a fragment or length of nucleic acid that is sufficient to detect the presence of the PCA3 gene in a DNA preparation from a normal or affected individual, the absence of such gene, or an altered physical property of such gene (such as a change in electrophoretic migration pattern). Preferably, any of the probes as described above are used.

Prenatal diagnosis can be performed when desired, using any known method to obtain fetal cells, including amniocentesis, chorionic villous sampling (CVS), and fetoscopy. Prenatal chromosome analysis can be used to determine if the portion of the chromosome possessing the normal PCA3 gene is present in a heterozygous state.

XI. Therapeutic Treatments

A. Therapeutic Nucleic Acids

A therapeutic nucleic acid as a therapeutic agent can have, but is not limited to, at least one of the following therapeutic effects on a target cell: inhibiting transcription of a DNA sequence; inhibiting translation of an RNA sequence; inhibiting reverse transcription of an RNA or DNA sequence; inhibiting a post-translational modification of a protein; inducing transcription of a DNA sequence; inducing translation of an RNA sequence; inducing reverse transcription of an RNA or DNA sequence; inducing a post-translational modification of a protein; transcription of the nucleic acid as an RNA; translation of the nucleic acid as a protein or enzyme; and incorporating the nucleic acid into a chromosome of a target cell for constitutive or transient expression of the therapeutic nucleic acid.

Therapeutic effects of therapeutic nucleic acids can include, but are not limited to: turning off a defective gene or processing the expression thereof, such as antisense RNA or DNA; inhibiting viral replication or synthesis; gene therapy as expressing a heterologous nucleic acid encoding a therapeutic protein or correcting a defective protein; modifying a defective or underexpression of an RNA such as an hnRNA, an mRNA, a tRNA, or an rRNA; encoding a drug or prodrug, or an enzyme that generates a compound as a drug or prodrug in pathological or normal cells expressing the chimeric receptor; and any other known therapeutic effects.

In the method of treating a PCA3-associated disease (preferably, prostate cancer) in a patient in need of such treatment, a PCA3 gene which is not indicative of a disease state can be provided to the cells of such patient in a manner and amount that permits the expression of the PCA3 protein provided by such gene, for a time and in a quantity sufficient to treat such patient. Preferably, gene replacement ("knock out") technology is used that would replace the disease causing PCA3 gene with a PCA3 gene which does not cause disease (specifically, prostate cancer).

Included as well in the invention are pharmaceutical compositions comprising an effective amount of at least one PCA3 antisense oligonucleotide, in combination with a pharmaceutically acceptable carrier. Such antisense oligos include, but are not limited to, at least one nucleotide sequence of 12-500 bases in length which is complementary to PCA3 exons 1, 2, 3, 4a-4-d; a DNA sequence of SEQ ID NO:1, 3, 4, or 6; or a DNA sequence encoding at least 4 amino acids of SEQ ID NO:2 or SEQ ID NO:7.

Alternatively, the PCA3 nucleic acid can be combined with a lipophilic carrier such as any one of a number of sterols including cholesterol, cholate and deoxycholic acid. A preferred sterol is cholesterol.

The PCA3 gene therapy nucleic acids and the pharmaceutical compositions of the invention can be administered by any means that achieve their intended purpose. For example, administration can be by parenteral, subcutaneous, intravenous, intramuscular, intra-peritoneal, or transdermal routes. The dosage administered will be dependent upon the age, health, and weight of the recipient, kind of concurrent treatment, if any, frequency of treatment, and the nature of the effect desired.

Compositions within the scope of this invention include all compositions wherein the PCA3 antisense oligonucleotide is contained in an amount effective to achieve decreased expression of at least one PCA3 gene. While individual needs vary, determination of optimal ranges of effective amounts of each component is within the skill of the art. Typically, the PCA3 nucleic acid can be administered to mammals, e.g. humans, at a dose of 0.005 to 1 mg/kg/day, or an equivalent amount of the pharmaceutically acceptable salt thereof, per day of the body weight of the mammal being treated.

Suitable formulations for parenteral administration include aqueous solutions of the PCA3 nucleic acid in water-soluble form, for example, water-soluble salts. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides. Aqueous injection suspensions can contain substances which increase the viscosity of the suspension include, for example, sodium carboxymethyl cellulose, sorbitol, and/or dextran. Optionally, the suspension can also contain stabilizers.

Many vector systems are known in the art to provide such delivery to human patients in need of a gene or protein missing from the cell. For example, retrovirus systems can be used, especially modified retrovirus systems and especially herpes simplex virus systems (Gage et al., U.S. Pat. No. 5,082,670). Such methods are provided for, in, for example, the teachings of Breakefield, X. A. et al., *The New Biologist* 3:203-218 (1991); Huang, Q. et al., *Experimental Neurology* 115:303-316 (1992); WO93/03743; WO90/0944; Taylor, WO 92/06693; Mulligan, R. C., *Science* 260:926-932 (1993); and Brown et al., "Retroviral Vectors," in *DNA Cloning: A*

Practical Approach, Volume 3, IRL Press, Washington, D.C. (1987). Delivery of a DNA sequence encoding a normally expressed PCA3 protein will effectively replace the PCA3 gene responsible for the disease state (ex. prostate cancer).

The means by which the vector carrying the nucleic acid can be introduced into the cell include but is not limited to, microinjection, electroporation, transduction, or transfection using DEAE-Dextran, lipofection, calcium phosphate or other procedures known to one skilled in the art (*Molecular Cloning, A Laboratory Manual*, Sambrook et al., eds., Cold Spring Harbor Press, Plainview, N.Y. (1989)).

In another embodiment of this invention, a normal PCA3 gene is expressed as a recombinant gene in a cell, so that the cells can be transplanted into a mammal, preferably a human in need of gene therapy. To provide gene therapy to an individual, a genetic sequence which encodes for all or part of the PCA3 gene is inserted into a vector and introduced into a host cell.

Further gene therapy methods which can be used to transfer nucleic acid to a patient are set forth in Chatterjee and Wong, *Current Topics in Microbiol. and Immuno.,* 218: 61-73 (1996); Zhang, *J. Mol. Med.* 74:191-204 (1996); Schmidt-Wolf and Schmidt-Wolf, *J. of Hematotherapy* 4:551-561 (1995); Shaughnessy et al., *Seminars in Oncology* 23(1): 159-171 (1996); and Dunbar *Annu. Rev. Med.* 47:11-20 (1996).

Specificity for gene expression in prostate cancer cells can be conferred by using appropriate cell-specific regulatory sequences, such as cell-specific enhancers and promoters.

Thus, gene therapy can be used to alleviate PCA3 related pathology by inhibiting the inappropriate expression of a particular form of PCA3. Moreover, gene therapy can be used to alleviate such pathologies by providing the appropriate expression level of a particular form of PCA3. In this case, particular PCA3 nucleic acid sequences can be coded by DNA or RNA constructs which are administered in the form of viruses, as described above.

B. Antagonists and Agonists of PCA3

The ability of antagonists and agonists of PCA3 to interfere or enhance the activity of PCA3 can be evaluated with cells containing PCA3. An assay for PCA3 activity in cells can be used to determine the functionality of the PCA3 protein in the presence of an agent which may act as antagonist or agonist, and thus, agents that interfere or enhance the activity of PCA3 are identified.

The agents screened in the assays can be, but are not limited to, antibodies, peptides, carbohydrates, vitamin derivatives, or other pharmaceutical agents. These agents can be selected and screened 1) at random, 2) by a rational selection or 3) by design using for example, protein or ligand modeling techniques (preferably, computer modeling).

For random screening, agents such as antibodies, peptides, carbohydrates, pharmaceutical agents and the like are selected at random and are assayed for their ability to bind to or stimulate/block the activity of the PCA3 protein.

Alternatively, agents may be rationally selected or designed. As used herein, an agent is said to be "rationally selected or designed" when the agent is chosen based on the configuration of the PCA3 protein.

In one embodiment, the present invention relates to a method of screening for an antagonist or agonist which stimulates or blocks the activity of PCA3 comprising:

(a) incubating a cell expressing PCA3 with an agent to be tested; and (b) assaying the cell for the activity of the PCA3 protein by measuring the agents effect on ATP binding of PCA3.

Any cell may be used in the above assay so long as it expresses a functional form of PCA3 and the PCA3 activity can be measured. The preferred expression cells are eukaryotic cells or organisms. Such cells can be modified to contain DNA sequences encoding PCA3 using routine procedures known in the art. Alternatively, one skilled in the art can introduce mRNA encoding the PCA3 protein directly into the cell.

Using PCA3 ligands (ligands including antagonists and agonists as described above) the present invention further provides a method for modulating the activity of the PCA3 protein in a cell. In general, ligands (antagonists and agonists) which have been identified to block or stimulate the activity of PCA3 can be formulated so that the ligand can be contacted with a cell expressing a PCA3 protein in vivo. The contacting of such a cell with such a ligand results in the in vivo modulation of the activity of the PCA3 proteins. So long as a formulation barrier or toxicity barrier does not exist, ligands identified in the assays described above will be effective for in vivo use.

In another embodiment, the present invention relates to a method of administering PCA3 or a PCA3 ligand (including PCA3 antagonists and agonists) to an animal (preferably, a mammal (specifically, a human)) in an amount sufficient to effect an altered level of PCA3 in the animal. The administered PCA3 or PCA3 ligand could specifically effect PCA3 associated functions. Further, since PCA3 is expressed in prostatic cancer cells, administration of PCA3 or PCA3 ligand could be used to alter PCA3 levels in such cells.

One skilled in the art will appreciate that the amounts to be administered for any particular treatment protocol can readily be determined. The dosage should not be so large as to cause adverse side effects, such as unwanted cross-reactions, anaphylactic reactions, and the like. Generally, the dosage will vary with the age, condition, sex and extent of disease in the patient, counter indications, if any, and other such variables, to be adjusted by the individual physician. Dosage can vary from 0.001 mg/kg to 50 mg/kg of PCA3 or PCA3 ligand, in one or more administrations daily, for one or several days. PCA3 or PCA3 ligand can be administered parenterally by injection or by gradual perfusion over time. It can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases and the like. See, generally, *Remington's Pharmaceutical Science,* 16th Ed., Mack Eds. (1980).

In another embodiment, the present invention relates to a pharmaceutical composition comprising PCA3 or PCA3 ligand in an amount sufficient to alter PCA3 associated activity, and a pharmaceutically acceptable diluent, carrier, or excipient. Appropriate concentrations and dosage unit sizes can be readily determined by one skilled in the art as described above (See, for example, *Remington's Pharmaceutical Sciences* (16th ed., Osol, A., Ed., Mack, Easton Pa. (1980) and WO 91/19008).

C. Immunotherapy

The present invention provides the above-described PCA3 antibodies (preferably, PCA3 murine antibodies and chimeric PCA3 murine-human antibodies, and fragments and regions thereof) which inhibit or neutralize PCA3 biological activity in vivo and are specific for PCA3. These antibodies can be used for therapeutic purposes in subjects having pathologies or conditions associated with the presence of aberrant PCA3 expression. Antibodies, and fragments, regions and derivatives thereof, of the present invention preferably contain at least one region which recognizes an epitope of PCA3 which has inhibiting and/or neutralizing biological activity in vivo.

Treatment comprises parenterally administering a single or multiple doses of the antibody, fragment or derivative. Preferred for human pharmaceutical use are high affinity potent PCA3-inhibiting and/or neutralizing murine and chimeric antibodies, fragments and regions of this invention.

Monoclonal antibodies of the present invention may be administered by any means that enables the active agent to reach the agent's site of action in the body of a mammal. Because proteins are subject to being digested when administered orally, parenteral administration, i.e., intravenous, subcutaneous, intramuscular, would ordinarily be used to optimize absorption.

Monoclonal antibodies of the present invention may be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Dosage forms (composition) suitable for internal administration generally contain from about 1 milligram to about 500 milligrams of active ingredient per unit. In these pharmaceutical compositions the active ingredient will ordinarily be present in an amount of about 0.5-95% by weight based on the total weight of the composition.

For parenteral administration, the antibody can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of Remington's Pharmaceutical Sciences, A. Osol, a standard reference text in this field.

The murine and chimeric antibodies, fragments and regions of this invention, their fragments, and derivatives can be used therapeutically as immunoconjugates (see for review: Dillman, R. O., *Ann. Int. Med.* 111:592-603 (1989)). They can be coupled to cytotoxic proteins, including, but not limited to Ricin-A, *Pseudomonas* toxin, and Diphtheria toxin. Toxins conjugated to antibodies or other ligands, are known in the art (see, for example, Olsnes, S. et al., *Immunol. Today* 10:291-295 (1989)). Plant and bacterial toxins typically kill cells by disrupting the protein synthetic machinery.

The antibodies of this invention can be conjugated to additional types of therapeutic moieties including, but not limited to, radionuclides, cytotoxic agents and drugs. Examples of radionuclides which can be coupled to antibodies and delivered in vivo to sites of antigen include $^{212}$Bi, $^{131}$I, $^{186}$Re, and $^{90}$Y, which list is not intended to be exhaustive. The radionuclides exert their cytotoxic effect by locally irradiating the cells, leading to various intracellular lesions, as is known in the art of radiotherapy.

Cytotoxic drugs which can be conjugated to antibodies and subsequently used for in vivo therapy include, but are not limited to, daunorubicin, doxorubicin, methotrexate, and Mitomycin C. Cytotoxic drugs interfere with critical cellular processes including DNA, RNA, and protein synthesis. For a fuller exposition of these classes of drugs which are known in the art, and their mechanisms of action, see Goodman, A. G., et al., *Goodman and Gilman's THE PHARMACOLOGICAL BASIS OF THERAPEUTICS*, 7th Ed., Macmillan Publishing Co., 1985.

The antibodies of this invention may be advantageously utilized in combination with other monoclonal or murine and chimeric antibodies, fragments and regions, or with lymphokines or hemopoietic growth factors, etc., which serve to increase the number or activity of effector cells which interact with the antibodies.

XII. Transgenic PCA3 Non-Human Animals

Methods of Generating Transgenic Non-Human Animals

The non-human animals of the invention comprise any animal having a transgenic interruption or alteration of the endogenous gene(s) (knock-out animals) and/or into the genome of which has been introduced one or more transgenes that direct the expression of human PCA3. Also preferred are the introduction of antisense PCA3 nucleic acids.

Such non-human animals include vertebrates such as rodents, non-human primates, sheep, dog, cow, amphibians, reptiles, etc. Preferred non-human animals are selected from non-human mammalian species of animals, most preferably, animals from the rodent family including rats and mice, most preferably mice.

The transgenic animals of the invention are animals into which has been introduced by nonnatural means (i.e., by human manipulation), one or more genes that do not occur naturally in the animal, e.g., foreign genes, genetically engineered endogenous genes, etc. The nonnaturally introduced genes, known as transgenes, may be from the same or a different species as the animal but not naturally found in the animal in the configuration and/or at the chromosomal locus conferred by the transgene. Transgenes may comprise foreign DNA sequences, i.e., sequences not normally found in the genome of the host animal. Alternatively or additionally, transgenes may comprise endogenous DNA sequences that are abnormal in that they have been rearranged or mutated in vitro in order to alter the normal in vivo pattern of expression of the gene, or to alter or eliminate the biological activity of an endogenous gene product encoded by the gene. (Watson, J. D., et al., in *Recombinant DNA*, 2d Ed., W.H. Freeman & Co., New York (1992), pages 255-272; Gordon, J. W., *Intl. Rev. Cytol.* 115:171-229 (1989); Jaenisch, R., *Science* 240:1468-1474 (1989); Rossant, J., *Neuron* 2:323-334 (1990)).

The transgenic non-human animals of the invention are produced by introducing transgenes into the germline of the non-human animal. Embryonic target cells at various developmental stages are used to introduce the transgenes of the invention. Different methods are used depending on the stage of development of the embryonic target cell(s).

1. Microinjection of zygotes is the preferred method for incorporating transgenes into animal genomes in the course of practicing the invention. A zygote, a fertilized ovum that has not undergone pronuclei fusion or subsequent cell division, is the preferred target cell for microinjection of transgenic DNA sequences. The murine male pronucleus reaches a size of approximately 20 micrometers in diameter, a feature which allows for the reproducible injection of 1-2 picoliters of a solution containing transgenic DNA sequences. The use of a zygote for introduction of transgenes has the advantage that, in most cases, the injected transgenic DNA sequences will be incorporated into the host animal's genome before the first cell division (Brinster, et al., *Proc. Natl. Acad. Sci.* (USA) 82:4438-4442 (1985)). As a consequence, all cells of the resultant transgenic animals (founder animals) stably carry an incorporated transgene at a particular genetic locus, referred to as a transgenic allele. The transgenic allele demonstrates Mendelian inheritance: half of the offspring resulting from the cross of a transgenic animal with a non-transgenic animal will inherit the transgenic allele, in accordance with Mendel's rules of random assortment.

2. Viral integration can also be used to introduce the transgenes of the invention into an animal. The developing embryos are cultured in vitro to the developmental stage known as a blastocyst. At this time, the blastomeres may be infected with appropriate retroviruses (Jaenich, R., *Proc. Natl. Sci.* (USA) 73:1260-1264 (1976)). Infection of the blastomeres is enhanced by enzymatic removal of the zona pellucida (Hogan, et al., in *Manipulating the Mouse Embryo*, Cold Spring Harbor Press, Cold Spring Harbor, N.Y. (1986)). Transgenes are introduced via viral vectors which are typically replication-defective but which remain competent for integration of viral-associated DNA sequences, including transgenic DNA sequences linked to such viral sequences, into the host animal's genome (Jahner, et al., *Proc. Natl. Acad. Sci.* (USA) 82:6927-6931 (1985); Van der Putten, et al., *Proc. Natl. Acad. Sci.* (USA) 82:6148-6152 (1985)). Transfection is easily and efficiently obtained by culture of blastomeres on a mono-layer of cells producing the transgene-containing viral vector (Van der Putten, et al., *Proc. Natl. Acad. Sci.* (USA) 82:6148-6152 (1985); Stewart, et al., *EMBO Journal* 6:383-388 (1987)). Alternatively, infection may be performed at a later stage, such as a blastocoele (Jahner, D., et al., *Nature* 298:623-628 (1982)). In any event, most transgenic founder animals produced by viral integration will be mosaics for the transgenic allele; that is, the transgene is incorporated into only a subset of all the cells that form the transgenic founder animal. Moreover, multiple viral integration events may occur in a single founder animal, generating multiple transgenic alleles which will segregate in future generations of offspring. Introduction of transgenes into germline cells by this method is possible but probably occurs at a low frequency (Jahner, D., et al., *Nature* 298:623-628 (1982)). However, once a transgene has been introduced into germline cells by this method, offspring may be produced in which the transgenic allele is present in all of the animal's cells, i.e., in both somatic and germline cells.

3. Embryonic stem (ES) cells can also serve as target cells for introduction of the transgenes of the invention into animals. ES cells are obtained from pre-implantation embryos that are cultured in vitro (Evans, M. J., et al., *Nature* 292:154-156 (1981); Bradley, M. O., et al., *Nature* 309:255-258 (1984); Gossler, et al., *Proc. Natl. Acad. Sci.* (USA) 83:9065-9069 (1986); Robertson et al., *Nature* 322:445-448 (1986); Robertson, E. J., in *Teratocarcinomas and Embryonic Stem Cells: A Practical Approach*, Robertson, E. J., ed., IRL Press, Oxford (1987), pages 71-112). ES cells, which are commercially available (from, e.g., Genome Systems, Inc., St. Louis, Mo.), can be transformed with one or more transgenes by established methods (Lovell-Badge, R. H., in *Teratocarcinomas and Embryonic Stem Cells: A Practical Approach*, Robertson, E. J., ed., IRL Press, Oxford (1987), pages 153-182). Transformed ES cells can be combined with an animal blastocyst, whereafter the ES cells colonize the embryo and contribute to the germline of the resulting animal, which is a chimera (composed of cells derived from two or more animals) (Jaenisch, R., *Science* 240:1468-1474 (1988); Bradley, A., in *Teratocarcinomas and Embryonic Stem Cells: A Practical Approach, Robertson*, E. J., ed., IRL Press, Oxford (1987), pages 113-151). Again, once a transgene has been introduced into germline cells by this method, offspring may be produced in which the transgenic allele is present in all of the animal's cells, i.e., in both somatic and germline cells.

However it occurs, the initial introduction of a transgene is a Lamarckian (non-Mendelian) event. However, the transgenes of the invention may be stably integrated into germ line cells and transmitted to offspring of the transgenic animal as Mendelian loci. Other transgenic techniques result in mosaic transgenic animals, in which some cells carry the transgenes and other cells do not. In mosaic transgenic animals in which germ line cells do not carry the transgenes, transmission of the transgenes to offspring does not occur. Nevertheless, mosaic transgenic animals are capable of demonstrating phenotypes associated with the transgenes.

Transgenes may be introduced into non-human animals in order to provide animal models for human diseases. Transgenes that result in such animal models include, e.g., transgenes that encode mutant gene products associated with an inborn error of metabolism in a human genetic disease and transgenes that encode a human factor required to confer susceptibility to a human pathogen (i.e., a bacterium, virus, or other pathogenic microorganism) (Leder et al., U.S. Pat. No. 5,175,383 (Dec. 29, 1992); Kindt et al., U.S. Pat. No. 5,183,949 (Feb. 2, 1993); Small et al., *Cell* 46:13-18 (1986); Hooper et al., *Nature* 326:292-295 (1987); Stacey et al., *Nature* 332:131-136 (1988); Windle et al., *Nature* 343:665-669 (1990); Katz et al., *Cell* 74:1089-1100 (1993)). Transgenically introduced mutations comprise null ("knock-out") alleles in which a DNA sequence encoding a selectable and/or detectable marker is substituted for a genetic sequence normally endogenous to a non-human animal. Resultant transgenic non-human animals that are predisposed to a disease, or in which the transgene causes a disease, may be used to identify compositions that induce the disease and to evaluate the pathogenic potential of compositions known or suspected to induce the disease (Berns, A. J. M., U.S. Pat. No. 5,174,986 (Dec. 29, 1992)), or to evaluate compositions which may be used to treat the disease or ameliorate the symptoms thereof (Scott et al., WO 94/12627 (1994)).

Offspring that have inherited the transgenes of the invention are distinguished from littermates that have not inherited transgenes by analysis of genetic material from the offspring for the presence of biomolecules that comprise unique sequences corresponding to sequences of, or encoded by, the transgenes of the invention. For example, biological fluids that contain polypeptides uniquely encoded by the selectable marker of the transgenes of the invention may be immunoassayed for the presence of the polypeptides. A more simple and reliable means of identifying transgenic offspring comprises obtaining a tissue sample from an extremity of an animal, e.g., a tail, and analyzing the sample for the presence of nucleic acid sequences corresponding to the DNA sequence of a unique portion or portions of the transgenes of the invention, such as the selectable marker thereof. The presence of such nucleic acid sequences may be determined by, e.g., hybridization ("Southern") analysis with DNA sequences corresponding to unique portions of the transgene, analysis of the products of PCR reactions using DNA sequences in a sample as substrates and oligonucleotides derived from the transgene's DNA sequence, etc.

The present invention is described in further detail in the following non-limiting examples.

EXAMPLE 1

Isolation and Characterization of PCA3 cDNA and Genomic DNA

In order to identify new markers for prostate cancer, a differential display analysis (Liang et al., Science 257: 967-971 (1992)) was used to identify genes overexpressed in prostatic carcinomas in comparison to normal prostate; total RNA from normal, benign hyperplastic and malignant prostatic tissue from the same patients was extracted. Using twenty different combinations of primers (four anchored primers, five arbitrary primers), eleven apparently differentially expressed mRNAs were identified (i.e., consistently overexpressed in all carcinomas studied and not expressed in normal or BPH tissue). The complementary DNA (cDNA) fragments were used as probes for Northern blot analysis to confirm the consistent overexpression in the prostatic tumors used for the differential display. One of the probes (named DD3, a 486 bp cDNA) detected two major transcripts (2.3 and 4.0 kb) that are highly overexpressed in 47 of 50 human prostatic tumors studied, whereas no (or very low levels of) expression of these transcripts was found in normal or BPH tissue from the same patients.

To obtain a full length cDNA clone, a cDNA library was constructed using mRNA isolated from human primary prostatic tumor tissue. 250 positive DD3 related clones were obtained from screening this library. 80 clones were purified and the nucleotide sequence of these clones was determined by automated sequence analysis.

A genomic library constructed of human placenta genomic DNA cloned in λFIX2 was screened using DD3 as a probe. Four different clones were obtained, two of them located towards the 5' end of the gene (λFIX-ME3 and -ME4) and two clones located towards the 3' end of the gene (λFIX-ME1 and -ME2). The 5' end of λFIX-ME4 was subcloned and used as a probe to screen the genomic library. Three new, unique clones were isolated (λFIX-1H1, IH2, and IH6).

From the 80 analyzed cDNA clones, at least four different transcripts were shown to be present due to alternative splicing or alternative polyadenylation. Sequence analysis of the genomic clones as compared to the cDNA clones revealed the genomic structure of the PCA3 gene. Three introns and 4 exons are present. The first intron is approximately 20 kb in length.

The first cDNA species is found in approximately 5% of the cDNA clones and contains exons 1, 2, 3, 4a and 4b (poly-adenylation after 4b is preceded by a real consensus poly-A-addition signal) (FIG. 1).

The second cDNA species, found in approximately 15% of the cDNA cloned, contains exons 1, 3, 4a, 4b and 4c, arises by alternative splicing of the second exon (not present in this cDNA) and terminates at a different (real consensus) poly-A-addition signal (FIG. 1).

The third cDNA species contains exons 1, 3, 4a, and 4b and is the most common one found (approximately 65% of 80 clones) (FIG. 1). This cDNA is most likely responsible for the most prominent transcript seen by Northern blot analysis (2 kb).

The fourth cDNA species detected contains exons 1, 3, and 4a representing about 15% of clones, and terminates after 4a, which is the original DD3 clone stop site (FIG. 1). The poly-A-addition signal present here is close to the consensus sequence.

PCA3 is a gene wherein significant alternative splicing (as well as alternative poly-adenylation) occurs, as evidenced by the differently sized transcripts observed on Northern blots and the different types of clones identified. As mentioned previously, other splicing variants can be identified, as virtually every combination of exons is possible. For instance, a cDNA clone having exons 2, 3, 4a, 4b, and 4c has recently been identified. Indeed, it appears that clones representing virtually all possible exon combinations have been isolated.

One such splicing variant was identified by sequencing a clone named λDD3.6. λDD3.6 is a λgt11 clone identified and isolated upon screening of a cDNA library made from prostate RNA of a 25 year old male (obtained from Clonetech) with a PCA3 probe. λDD3.6 contains exon 3, 4a, 4b, 4c, and 4d. However, this cDNA clone also contains intron sequences (part of intron 2, as well as intron 3).

A comparison of the two deposited clones PMB9 and λDD3.6 is shown in FIG. 3.

Figure 2:
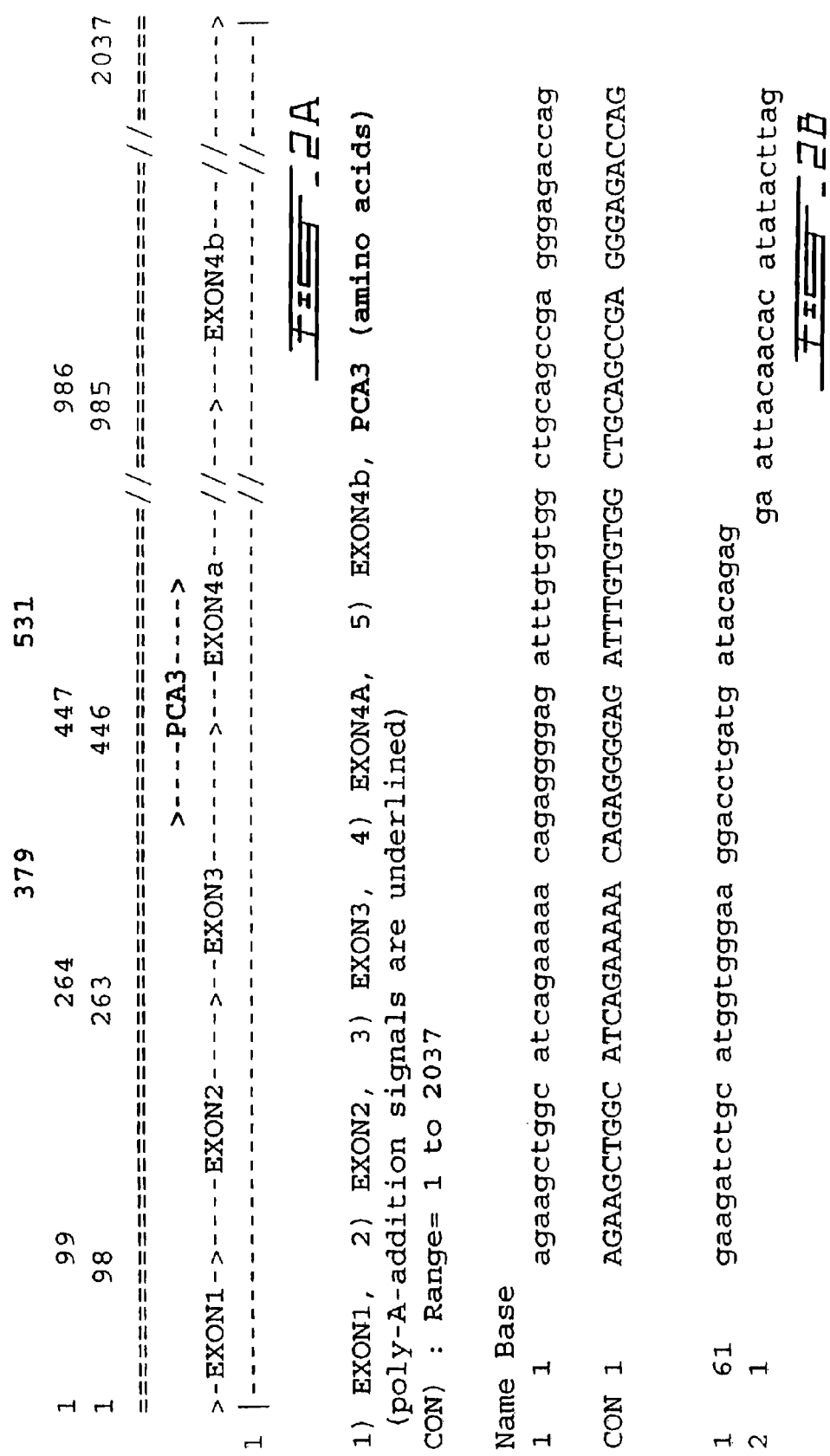
FIG. 2A-J, (A) a PCA3 cDNA structure; (B)-(J) a PCA3 nucleotide and amino acid cDNA sequence (SEQ ID NOs:1 and 2).

Different combinations of exons were examined by computer analysis to identify open reading frames (ORFs) and to predict the protein encoding region. The longest ORF was also the most highly likely protein encoding region. The longest ORF of 153 nucleotides encodes a small peptide of 51 amino acids, PCA3. PCA3 is encoded by part of exon 3 and 4a. The small size of the protein suggests that the protein most likely functions as a messenger molecule and has the potential to be secreted from the cells. The nucleotide sequence of exons 1-4-a-d and the amino acid sequence of PCA3 are shown in FIG. 2 and FIG. 5 (SEQ ID NO:1 and 6 and 2 and 7, respectively).

It will be recognized by the person of ordinary skill, that a cDNA clone comprising the nucleic acid sequence presented in SEQ ID NO:6 and shown in FIG. 5 can be obtained as previously described by isolating and characterizing PCA3 cDNA clones. For example, and as commonly known in the art, probes which are specific to at least one of the 5' end, exon 1, 2, 3, 4a, 4b, 4c and 4d can be further used to increase the probability of having a full-length PCA3 cDNA clone. 96-well plates, for example, can be used to screen a large number of PCA3 positive cDNA clones, using the probes mentioned above. Of course, PCA3 positive clones can also be sequenced, as commonly known and as described herein, until a desired cDNA clone is obtained.

In addition it is also possible to obtain a cDNA clone comprising the sequence shown in SEQ ID NO:6 and shown in FIG. 5, using PCA3 specific primers and an amplifying method such as PCR. For example, PCR technology with primers specific for the ultimate 5' and 3' end of the PCA3 cDNA, could be used to amplify a desired product (almost 4 kb) from RNA, isolated for example from prostatic tumors, and clone the PCR products. However, since PCR amplification may introduce mistakes, a sequencing of the complete cDNA would most likely be required.

As well known to the person of ordinary skill, a cDNA clone comprising the sequence shown in SEQ ID NO:6 and shown in FIG. 5 can also be constructed using the clones described herein (or newly isolated ones) and conventional genetic engineering methods.

For example, such a full length cDNA clone can be constructed using the deposited clones pMB9 and λDD3.6. A non-limiting example of a strategy to construct such a cDNA clone comprising the nucleic acid sequence of SEQ ID NO:6 and FIG. 5, is described below.

λDD3.6 phage DNA is digested to completion with NdeI, and the approximately 2 kb NdeI fragment isolated from an agarose gel. This fragment contains part of PCA3 exon 4b, exons 4c+4d and about 50 nucleotides of phage DNA. The ends of this 2 kb fragment are then filled in with Klenow-fragment DNA polymerase and dNTPs, the blunt-ended fragment are then ligated into the HincII/SmaI sites of Bluescript SK. The loss of the HindIII site of Bluescript by the HincII and SmaI digestion is essential for further cloning steps in this particular strategy (see below). It is to be noted that NdeI sites are also present in phage λgt11, giving rise to several additional fragments, some of which are close to 2 kb (i.e., a 1.8 kb and a 2.5 kb fragment). Nevertheless, it is straight forward to separate these different bands on an agarose gel. The correct orientation of insertion of the blunt-ended 2 kb NdeI fragment of IDD3.6 into Bluescript (termed construct PCA3-X) can be verified by a single SacI digestion, which should yield a ~0.45 and ~4.5 kb fragment by Ethidium-bromide staining of agarose gels. Sequence analysis may be performed to confirm the identity of the PCA3 insert.

The PCA3-X construct is then digested to completion with HindIII and BamHI and a 4.8 kb vector-insert isolated from an agarose gel. This results in the removal of ~0.2 kb of DNA from the insert. pMB9 can be simultaneously digested to completion with BamHI and HindIII and the 1.9 kb insert (containing PCA3 exons 1, 2, 3, 4a and most of exon 4b) isolated from an agarose gel. The pMB9-derived insert is ligated into the BamHI/HindIII site of the PCA3-X construct. The resulting construct, PCA3-Y contains the complete cDNA of PCA3, except for the first 22 nucleotides of exon1 (see below and FIG. 4). These 22 nucleotides can be added to the PCA3 cDNA by cutting the PCA3-Y construct and the oligo-(74)-mer (SEQ ID NO:8) to completion with BamHI and PstI and ligating the oligomer in construct PCA3-Y, resulting in construct PCA3-Z. Nucleotide sequence analysis can be performed to verify that the oligo was properly ligated (i.e. to confirm that just one oligo was ligated and not a whole array of oligos). Of course, a sequencing of the resulting cDNA in PCA3-Z, can be performed to verify the integrity of the nucleic acid sequence.

Screening of a somatic cell hybrid panel revealed that the gene encoding PCA3 is located on human chromosome 9. Using a mixture of four PCA3-related genomic clones as a probe to hybridize to metaphase chromosomes of human lymphocytes, PCA3 was mapped to 9q21-22 (See also, FIG. 1).

The conservation of PCA3 gene during evolution was studied by Southern blot analysis and revealed that a homolog of this gene is present in monkey, cow, horse, sheep, goat and pig. The gene is also present in dog and cat. By comparison, the gene encoding PSA is only found in primates.

EXAMPLE 2

Prostate Specific Expression of PCA3

Upon developing PCA3 specific primers, RT-PCR analysis was performed using RNA from several normal human tissues. At 40 cycles of PCR, PCA3 related products in normal prostate and BPH tissues were amplified. PCA3 expression is very prostate specific since no PCA3 product could be amplified under these conditions in the following normal human tissues: artery, brain, breast, bladder, colon, duodenum, heart, liver, lung, ovary, pancreas, placenta, seminal vesicles, skeletal muscle, skin, spinal cord, spleen and testis. Also in the human prostate cancer cell lines ALVA-31, DU145, JCA-1, PPC-1, PC3, and TSU-Pr1 no PCA3 related PCR product could be detected. In the cell line LNCaP a product can be obtained after 40 cycles of PCR (whereas under the same conditions a product can be obtained in prostatic tumors within 20 cycles). The technology used to assess the prostate specific expression of PCA3 can be adapted in a diagnostic test for prostate cancer. In addition, it can be adapted to the identification of the prostatic origin of a metastase.

Furthermore, a semi-quantitative RT-PCR analysis to compare the expression of PCA3 to that of PSA (prostate-specific antigen) and PSM (prostate-specific membrane antigen) and to establish if PCA3-RT-PCR analysis can be used to distinguish malignant from benign prostatic specimens was performed. After quantification of the RT-reaction, 10 ng of cDNA was used for the PCR reaction and as a control, beta-2 microglobulin was also examined. PCA3 products found allowed a clear distinction between benign and malignant specimens in 23 of 25 cases studied whereas PSA and PSM could not make this distinction: approximately equal amounts of product were found in normal and tumor samples. The expression of PSA and PCA3 was also compared by Northern blot analysis, which clearly shows the higher tumor-specificity of PCA3. At least a 20-fold overexpression of PCA3 in prostatic carcinomas as compared to normal or BPH tissues is observed. This is distinctly different from expression of PSM and PSA, both of which are decreased in malignant versus benign tissues. Thus, PCA3 appears to be a good marker for diagnostic of prostate cancer.

An ideal tumor marker for prostate cancer should not only be able to positively distinguish between benign and malignant tissues but also be able to predict clinical outcome (cure or progression) of patients afflicted with this disease. Data has shown that indeed, the level of expression of PCA3 tends to be positively correlated with tumor grade.

RISH (and eventually immunohistochemistry) is used to establish whether or not there is correlation between overexpression of PCA3, tumor grade, stage, and clinical outcome. For both the paraffin-embedded and frozen specimens, long-term clinical follow-up is available. Using computer-assisted image analysis, quantitation of PCA3 expression levels as detected by RISH is performed and this is normalized to an external reference (Tamimi et al., *Cancer Res.* 53: 5512-16 (1993); Tamimi et al., *B.J. Cancer* (1996)). A multivariate regression analysis including Gleason: grade, pathological tumor stage, clinical tumor stage, PSA levels and PCA3 expression will be used to establish whether PCA3 is an accurate predictor of progression and has (additional) prognostic value.

Reverse transcriptase polymerase chain reaction (RT-PCR) assays have been developed to detect occult hematogenous micrometastatic cells that might otherwise have gone undetected by presently available staging modalities. Such RT-PCR assays have already been performed in patients with prostate cancer and other malignancies. A highly sensitive (nested) RT-PCR assay (or other types of amplification assays including without being limited to NASBA, PCR, QB rep., SOA, TMA, and LCR (Winn-Deen, *J. Clin., Liquid Assay* 19: 21-26 (1996)) can be used to detect prostate cancer cells in the circulating blood of prostate: cancer patients to identify patients at risk for having or developing metastases. Experiments will include appropriate controls (e.g. β-2-microglobulin) and will be performed in a semi-quantitative way (i.e., quantify the cDNA synthesis and use equal amounts of input for the PCR analysis).

The molecular staging studies will be performed in the larger context of the BIOMED II program (*Markers for Prostate Cancer*). In this extensive collaborative study, PSA and PSM will be studied as well as other potentially interesting markers for prostate cancer. Blood samples are already being collected from patients that are diagnosed with prostatic disease in the participating institutions. An optimization of the collecting and handling of blood samples from patients for the detection of circulating tumor cells has been initiated. The use for example of Vacutainer™ CPT-tubes (BecktonDickinson) for blood collection and purification of peripheral blood leukocytes in combination with a Trizol™ RNA-extraction procedure (guanidinium thiocyanate based) resulted in the preparation of RNA qualitatively and quantitatively suitable for PCR analysis. The use of PCA3-specific primers, to amplify PCA3 transcripts in RNA extracted from blood from prostate cancer patients, revealed that the presence of prostate cancer cells in the blood circulation, of not only patients with proven metastases, but also of patients with assumed localized disease, could be detected. More extensive studies on a larger patient population and a correlation with clinical data and follow-up will be carried out to determine the prognostic value of PCA3 for the individual prostate cancer patient.

Nested RT-PCR analysis (or similar amplification methods) should prove instrumental in determining whether there are any organs (not yet tested) that express PCA3. For example, Cowper's gland (same embryonic origin as the prostate) and also skene's gland (female "homologue" to the prostate) will be tested for PCA3.

In one "normal" prostate tissue specimen that contained 10% of tumor cells, PCA3 expression was detected indicating the high sensitivity of PCA3 as a tumor marker. In this manner, PCA3 expression was also detected in a few BPH samples that were subsequently found to contain small areas of tumor cells. The level of expression of PCA3 in prostatic cancers shows a trend towards a positive correlation with tumor grade. These data are based on analysis of autoradiographs resulting from Northern blot hybridization.

The observation that PCA3 expression seems to increase with loss of differentiation is different from what is reported for PSA, since PSA expression levels decrease with loss of differentiation (Hakalahti et al., *Int. J. Cancer* 55:590-597 (1993)). There is at least 20-fold overexpression of PCA3 in prostatic carcinomas in comparison to normal or BPH tissues. This is distinctly different from the expression of PSA which is reported to decrease in malignant versus benign tissues. PCA3 expression was detected in 4 of 4 metastases studied.

EXAMPLE 3

Identification of a Transcription Start Site of PCA3

Figure 4:
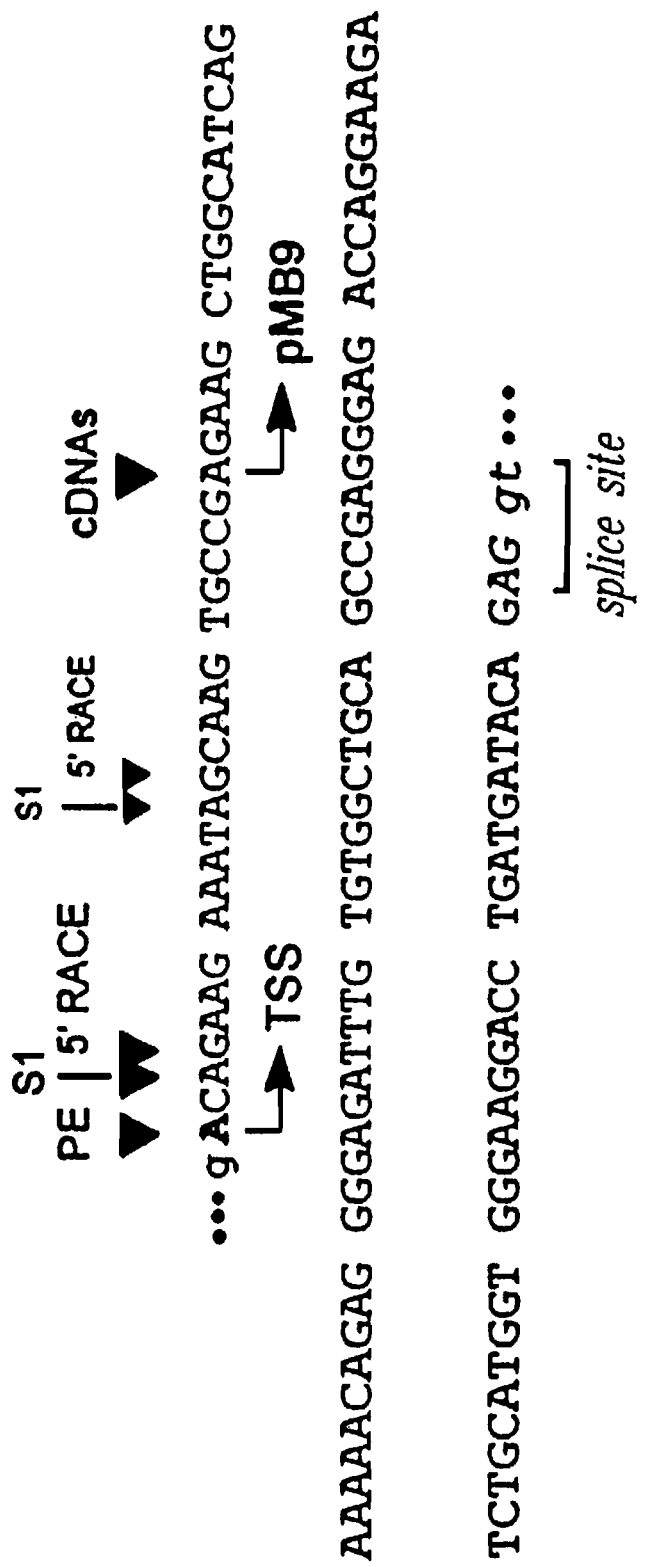
FIG. 4 shows the location of a transcription start site (TSS) of PCA3. The transcription start site was determined by primer extension (PE), S1-nuclease mapping (S1), and 5' Rapid Amplification of cDNA Ends (RACE) assays. The sequence in FIG. 4 (SEQ ID NO: 9) is as set forth between nucleotides 1 and 120 of SEQ ID NO:6 with a "g" nucleotide and a "gt" dinucleotide at the 5' and 3' ends respectively.

In order to determine the transcription start site of PCA3 primer extension analysis, S1-nuclease mapping and 5'RACE (rapid amplification of cDNA ends) assays were performed. The major transcription start site was found to be located within a range of 4 nucleotides (FIG. 4).

The results of these experiments further lengthen the size of the cDNA in a 5' direction by a further 22 nt with respect to the cDNA sequence of pMB9 (SEQ ID NO:1 and FIG. 2). This additional 5' polynucleotide sequence is also shown in SEQ ID NO:6 and FIG. 5).

While the foregoing invention has been described in some detail for purposes of clarity and understanding, it will be appreciated by one skilled in the art from a reading of this disclosure that various changes in form and detail can be made without departing from the true scope of the invention and appended claims.

Although the present invention has been described hereinabove by way of preferred embodiments thereof, it can be modified, without departing from the spirit and nature of the subject invention as defined in the appended claims.

What is claimed is:

1. A method of determining whether a sample contains a PCA3 nucleic acid, comprising:
   a) contacting said sample with a nucleic acid molecule 10 to 100 nucleotides in length comprising a sequence of at least 10 consecutive nucleotides contained within SEQ ID NO:1, SEQ ID NO:3, SEQ ID NO:4, SEQ ID NO:6 or a sequence fully complementary thereto; and
   b) detecting binding of said nucleic acid molecule to the PCA3 nucleic acid, whereby it is determined that said sample contains the PCA3 nucleic acid.

2. The method of claim 1, wherein said sequence of at least 10 consecutive nucleotides contained within SEQ ID NO:1, SEQ ID NO:3, SEQ ID NO:4, SEQ ID NO:6 or a sequence fully complementary thereto is a sequence of at least 15 consecutive nucleotides contained within SEQ ID NO:1, SEQ ID NO:3, SEQ ID NO:4, SEQ ID NO:6 or a sequence fully complementary thereto.

3. The method of claim 2, wherein said oligonucleotide of 10 to 100 nucleotides in length is an oligonucleotide 10 to 50 nucleotides in length.

4. The method of claim 2, wherein said oligonucleotide of 10 to 100 nucleotides in length is an oligonucleotide 10 to 35 nucleotides in length.

5. The method of claim 2, wherein said oligonucleotide of 10 to 100 nucleotides in length is an oligonucleotide of 20 to 100 nucleotides in length.

6. The method of claim 2, wherein said sequence of at least 15 consecutive nucleotides contained within SEQ ID NO:1, SEQ ID NO:3, SEQ ID NO:4 or SEQ ID NO:6 encodes a plurality of consecutive amino acids of the predicted PCA3 polypeptide of SEQ ID NO:2.

7. The method of claim 6, wherein said nucleic acid molecule of 10 to 100 nucleotides in length is a nucleic acid molecule of 20 to 100 nucleotides in length.

8. The method of claim 2, wherein the detecting comprises detecting in a nucleic acid hybridization procedure, and wherein said nucleic acid molecule comprises a detectable label.

9. The method of claim 6, wherein the detecting comprises detecting in a nucleic acid hybridization procedure, and wherein said nucleic acid molecule comprises a detectable label.

10. The method of claim 6, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 381-400 of SEQ ID NO:1.

11. The method of claim 6, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 381-410 of SEQ ID NO:1.

12. The method of claim 6, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 401-420 of SEQ ID NO:1.

13. The method of claim 6, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 401-430 of SEQ ID NO:1.

14. The method of claim 6, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the PCA3 predicted polypeptide of SEQ ID NO:2 comprises nucleotides 427-446 of SEQ ID NO:1.

15. The method of claim 6, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 447-466 of SEQ ID NO:1.

16. A method of determining whether a sample contains a PCA3 nucleic acid, comprising:
   a) contacting said sample with a nucleic acid molecule 10 to 100 nucleotides in length comprising a sequence of at least 10 consecutive nucleotides contained within SEQ ID NO:1, SEQ ID NO:3, SEQ ID NO:4, SEQ ID NO:6 or a sequence fully complementary thereto,
   b) detecting binding of said nucleic acid molecule to the PCA3 nucleic acid,
   whereby it is determined that said sample contains the PCA3 nucleic acid, wherein said nucleic acid molecule does not specifically hybridize to nucleotides 511-985 of SEQ ID NO:1, nucleotides 346-820 of SEQ ID NO:3, nucleotides 346-820 of SEQ ID NO:4 or nucleotides 533-1007 of SEQ ID NO:6 under stringent conditions of 0.2×SSC and 0.1° SDS at 68 degrees C.

17. The method of claim 16, wherein said sequence of at least 10 consecutive nucleotides contained within SEQ ID NO:1, SEQ ID NO:3, SEQ ID NO:4, SEQ ID NO:6 or a sequence fully complementary thereto is a sequence of at least 15 consecutive nucleotides contained within SEQ ID NO:1, SEQ ID NO:3, SEQ ID NO:4, SEQ ID NO:6 or a sequence fully complementary thereto.

18. The method of claim 17, wherein said oligonucleotide of 10 to 100 nucleotides in length is an oligonucleotide 10 to 50 nucleotides in length.

19. The method of claim 17, wherein said oligonucleotide of 10 to 100 nucleotides in length is an oligonucleotide of 10 to 35 nucleotides in length.

20. The method of claim 17, wherein said oligonucleotide of 10 to 100 nucleotides in length is an oligonucleotide of 20 to 100 nucleotides in length.

21. The method of claim 17, wherein said sequence of at least 15 consecutive nucleotides contained within SEQ ID NO:1, SEQ ID NO:3, SEQ ID NO:4 or SEQ ID NO:6 encodes a plurality of consecutive amino acids of the predicted PCA3 polypeptide of SEQ ID NO:2.

22. The method of claim 21, wherein said nucleic acid molecule of 10 to 100 nucleotides in length is a nucleic acid molecule of 20 to 100 nucleotides in length.

23. The method of claim 17, wherein the detecting comprises detecting in a nucleic acid hybridization procedure, and wherein said nucleic acid molecule comprises a detectable label.

24. The method of claim 21, wherein the detecting comprises detecting in a nucleic acid hybridization procedure, and wherein said nucleic acid molecule comprises a detectable label.

25. The method of claim 21, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 381-400 of SEQ ID NO:1.

26. The method of claim 21, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 381-410 of SEQ ID NO:1.

27. The method of claim 21, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 401-420 of SEQ ID NO:1.

28. The method of claim 21, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 401-430 of SEQ ID NO:1.

29. The method of claim 21, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the PCA3 polypeptide of SEQ ID NO:2 comprises nucleotides 427-446 of SEQ ID NO:1.

30. The method of claim 21, wherein said sequence of at least 15 consecutive nucleotides contained within SEQ ID NO:1, SEQ ID NO:3, SEQ ID NO:4 or SEQ ID NO:6 that encodes said plurality of consecutive amino acids of the predicted PCA3 polypeptide of SEQ ID NO:2 comprises nucleotides 447-466 of SEQ ID NO:1.

31. The method of claim 1, wherein said sequence of at least 10 consecutive nucleotides is contained within a PCA3 exon sequence selected from the group consisting of:
   a) PCA3 exon 1, as set forth between nucleotides 1-98 of SEQ ID NO:1 or 1-120 of SEQ ID NO:6;
   b) PCA3 exon 2, as set forth between nucleotides 99-263 of SEQ ID NO:1 or 121-285 of SEQ ID NO:6;
   c) PCA3 exon 3, as set forth between nucleotides 264-446 of SEQ ID NO:1 or 286-468 of SEQ ID NO:6;
   d) PCA3 exon 4a, as set forth between nucleotides 447-985 of SEQ ID NO:1 or 469-1007 of SEQ ID NO:6;
   e) PCA3 exon 4b, as set forth between nucleotides 986-2037 of SEQ ID NO:1 or 1008-2066 of SEQ ID NO:6;
   f) PCA3 exon 4c, as set forth between nucleotides 2067-2622 of SEQ ID NO:6;
   g) PCA3 exon 4d, as set forth between nucleotides 2623-3582 of SEQ ID NO:6; and
   h) a combination of said PCA3 exon sequences of a) to g).

32. The method of claim 1, wherein said nucleic acid molecule is or is complementary to the polynucleotide sequence encoding the predicted PCA3 open reading frame (ORF) set forth from nucleotides 379 to 531 of SEQ ID NO:1 or from nucleotides 401 to 553 of SEQ ID NO:6.

* * * * *

SEQUENCE LISTING

```
<160> NUMBER OF SEQ ID NOS: 9

<210> SEQ ID NO 1
<211> LENGTH: 2037
<212> TYPE: DNA
<213> ORGANISM: Homo sapiens
<220> FEATURE:
<221> NAME/KEY: CDS
<222> LOCATION: (379)..(531)
<220> FEATURE:
<221> NAME/KEY: misc_feature
<222> LOCATION: (1472)..(1472)
<223> OTHER INFORMATION: N = any nucleotide
<220> FEATURE:
<221> NAME/KEY: misc_feature
<222> LOCATION: (1517)..(1517)
<223> OTHER INFORMATION: N = any nucleotide
<220> FEATURE:
<221> NAME/KEY: misc_feature
<222> LOCATION: (1563)..(1563)
<223> OTHER INFORMATION: N = any nucleotide

<400> SEQUENCE: 1
agaagctggc atcagaaaaa cagaggggag atttgtgtgg ctgcagccga gggagaccag      60
gaagatctgc atggtgggaa ggacctgatg atacagagga attacaacac atatacttag     120
```

```
tgtttcaatg aacaccaaga taaataagtg aagagctagt ccgctgtgag tctcctcagt      180
gacacagggc tggatcacca tcgacggcac tttctgagta ctcagtgcag caaagaaaga      240
ctacagacat ctcaatggca ggggtgagaa ataagaaagg ctgctgactt taccatctga      300
ggccacacat ctgctgaaat ggagataatt aacatcacta gaaacagcaa gatgacaata      360
taatgtctaa gtagtgac atg ttt ttg cac att tcc agc ccc ttt aaa tat       411
                    Met Phe Leu His Ile Ser Ser Pro Phe Lys Tyr
                      1               5                  10 cca cac aca cag gaa gca caa aag gaa gca cag aga tcc ctg gga gaa       459
Pro His Thr Gln Glu Ala Gln Lys Glu Ala Gln Arg Ser Leu Gly Glu
             15                  20                  25 atg ccc ggc cgc cat ctt ggg tca tcg atg agc ctc gcc ctg tgc ctg       507
Met Pro Gly Arg His Leu Gly Ser Ser Met Ser Leu Ala Leu Cys Leu
         30                  35                  40 gtc ccg ctt gtg agg gaa gga cat tagaaaatga attgatgtgt tccttaaagg      561
Val Pro Leu Val Arg Glu Gly His
         45                  50 atgggcagga aacagatcc tgttgtggat atttatttga acgggattac agatttgaaa      621
tgaagtcaca aagtgagcat taccaatgag aggaaaacag acgagaaaat cttgatggct      681
tcacaagaca tgcaacaaac aaaatggaat actgtgatga catgaggcag ccaagctggg      741
gaggagataa ccacggggca gagggtcagg attctggccc tgctgcctaa actgtgcgtt      801
cataaccaaa tcatttcata tttctaaccc tcaaaacaaa gctgttgtaa tatctgatct      861
ctacggttcc ttctgggccc aacattctcc atatatccag ccacactcat tttaatatt      921 tagttcccag atctgtactg tgacctttct acactgtaga ataacattac tcattttgtt      981
caaagaccct tcgtgttgct gcctaatatg tagctgactg ttttttcctaa ggagtgttct     1041 ggcccagggg atctgtgaac aggctgggaa gcatctcaag atctttccag ggttatactt     1101
actagcacac agcatgatca ttacggagtg aattatctaa tcaacatcat cctcagtgtc     1161
tttgcccata ctgaaattca tttcccactt ttgtgcccat tctcaagacc tcaaaatgtc     1221
attccattaa tatcacagga ttaacttttt tttttaacct ggaagaattc aatgttacat     1281
gcagctatgg gaatttaatt acatattttg ttttccagtg caaagatgac taagtccttt     1341
atccctcccc tttgtttgat tttttttcca gtataaagtt aaaatgctta gccttgtact     1401
gaggctgtat acagcacagc ctctccccat ccctccagcc ttatctgtca tcaccatcaa     1461
cccctcccat nysacctaaa caaaatctaa cttgtaattc cttgaacatg tcaggncata     1521
cattrttcct tctgcctgag aagctcttcc ttgtctctta antctagaat gatgtaaagt     1581
tttgaataag ttgactatct tacttcatgc aaagaaggga cacatatgag attcatcatc     1641
acatgagaca gcaaatacta aaagtgtaat ttgattataa gagtttagat aaatatatga     1701
aatgcaagak ccacagaggg aatgtttatg gggcacgttt gtaagcctgg gatgtgaagm     1761
aaaggcaggg aacctcatag tatcttatat aatatacttc atttctctat ctctatcaca     1821
atatccaaca agcttttcac agaattcatg cagtgcaaat ccccaaaggt aacctttatc     1881
catttcatgg tgagtgcgct ttagaatttt ggcaaatcat actggtcact tatctcaact     1941
ttgagatgtg tttgtccttg tagttaattg aaagaaatag ggcactcttg tgagccactt     2001
tagggttcac tcctggcaat aaagaattta caaaga                                2037

<210> SEQ ID NO 2
<211> LENGTH: 51
<212> TYPE: PRT
<213> ORGANISM: Homo sapiens
```

-continued

```
<400> SEQUENCE: 2

Met Phe Leu His Ile Ser Ser Pro Phe Lys Tyr Pro His Thr Gln Glu
1               5                   10                  15

Ala Gln Lys Glu Ala Gln Arg Ser Leu Gly Glu Met Pro Gly Arg His
            20                  25                  30

Leu Gly Ser Ser Met Ser Leu Ala Leu Cys Leu Val Pro Leu Val Arg
        35                  40                  45

Glu Gly His
    50

<210> SEQ ID NO 3
<211> LENGTH: 1872
<212> TYPE: DNA
<213> ORGANISM: Homo sapiens
<220> FEATURE:
<221> NAME/KEY: misc_feature
<222> LOCATION: (1307)..(1307)
<223> OTHER INFORMATION: N = any amino acid
<220> FEATURE:
<221> NAME/KEY: misc_feature
<222> LOCATION: (1352)..(1352)
<223> OTHER INFORMATION: N = any amino acid
<220> FEATURE:
<221> NAME/KEY: misc_feature
<222> LOCATION: (1398)..(1398)
<223> OTHER INFORMATION: N = any amino acid

<400> SEQUENCE: 3
agaagctggc atcagaaaaa cagaggggag atttgtgtgg ctgcagccga gggagaccag      60
gaagatctgc atggtgggaa ggacctgatg atacagaggt gagaaataag aaaggctgct    120
gactttacca tctgaggcca cacatctgct gaaatggaga taattaacat cactagaaac    180
agcaagatga caatataatg tctaagtagt gacatgtttt tgcacatttc cagccccttt    240
aaatatccac acacacagga agcacaaaag gaagcacaga gatccctggg agaaatgccc    300
ggccgccatc ttgggtcatc gatgagcctc gccctgtgcc tggtcccgct tgtgagggaa    360
ggacattaga aaatgaattg atgtgttcct taaaggatgg gcaggaaaac agatcctgtt    420
gtggatattt atttgaacgg gattacagat ttgaaatgaa gtcacaaagt gagcattacc    480
aatgagagga aaacagacga gaaaatcttg atggcttcac aagacatgca acaaacaaaa    540
tggaatactg tgatgacatg aggcagccaa gctggggagg agataaccac ggggcagagg    600
gtcaggattc tggccctgct gcctaaactg tgcgttcata accaaatcat ttcatatttc    660
taaccctcaa aacaaagctg ttgtaatatc tgatctctac ggttccttct gggcccaaca    720
ttctccatat atccagccac actcattttt aatatttagt tcccagatct gtactgtgac    780 cttttctacac tgtagaataa cattactcat tttgttcaaa gacccttcgt gttgctgcct    840
aatatgtagc tgactgtttt tcctaaggag tgttctggcc caggggatct gtgaacaggc    900
tgggaagcat ctcaagatct ttccagggtt atacttacta gcacacagca tgatcattac    960
ggagtgaatt atctaatcaa catcatcctc agtgtctttg cccatactga aattcatttc   1020 ccactttgt gcccattctc aagacctcaa aatgtcattc cattaatatc acaggattaa   1080 ctttttttt taacctggaa gaattcaatg ttacatgcag ctatgggaat ttaattacat   1140
attttgtttt ccagtgcaaa gatgactaag tcctttatcc ctccccttg tttgattttt   1200 tttccagtat aaagttaaaa tgcttagcct tgtactgagg ctgtatacag cacagcctct   1260
ccccatccct ccagccttat ctgtcatcac catcaacccc tccatnysa cctaaacaaa   1320 atctaacttg taattccttg aacatgtcag gncatacatt rttccttctg cctgagaagc   1380
```

```
tcttccttgt ctcttaantc tagaatgatg taaagttttg aataagttga ctatcttact      1440
tcatgcaaag aagggacaca tatgagattc atcatcacat gagacagcaa atactaaaag      1500
tgtaatttga ttataagagt ttagataaat atatgaaatg caagakccac agagggaatg      1560
tttatggggc acgtttgtaa gcctgggatg tgaagmaaag gcaggaacc tcatagtatc       1620 ttatataata tacttcattt ctctatctct atcacaatat ccaacaagct tttcacagaa      1680
ttcatgcagt gcaaatcccc aaaggtaacc tttatccatt tcatggtgag tgcgctttag      1740
aattttggca atcatactg gtcacttatc tcaactttga gatgtgtttg tccttgtagt       1800
taattgaaag aaatagggca ctcttgtgag ccactttagg gttcactcct ggcaataaag      1860
aatttacaaa ga                                                          1872

<210> SEQ ID NO 4
<211> LENGTH: 820
<212> TYPE: DNA
<213> ORGANISM: Homo sapiens

<400> SEQUENCE: 4
agaagctggc atcagaaaaa cagaggggag atttgtgtgg ctgcagccga gggagaccag        60
gaagatctgc atggtgggaa ggacctgatg atacagaggt gagaaataag aaaggctgct       120
gactttacca tctgaggcca cacatctgct gaaatggaga taattaacat cactagaaac       180
agcaagatga caatataatg tctaagtagt gacatgtttt tgcacatttc cagcccttt        240 aaatatccac acacacagga agcacaaaag gaagcacaga gatccctggg agaaatgccc       300
ggccgccatc ttgggtcatc gatgagcctc gccctgtgcc tggtcccgct tgtgagggaa       360
ggacattaga aaatgaattg atgtgttcct taaaggatgg gcaggaaaac agatcctgtt       420
gtggatattt atttgaacgg gattacagat ttgaaatgaa gtcacaaagt gagcattacc       480
aatgagagga aaacgacga gaaaatcttg atggcttcac aagacatgca acaaacaaaa        540
tggaatactg tgatgacatg aggcagccaa gctggggagg agataaccac ggggcagagg       600
gtcaggattc tggccctgct gcctaaactg tgcgttcata accaaatcat ttcatatttc       660
taaccctcaa acaaagctg ttgtaatatc tgatctctac ggttccttct gggcccaaca        720
ttctccatat atccagccac actcatttt aatatttagt tcccagatct gtactgtgac        780 cttctctacac tgtagaataa cattactcat tttgttcaaa                           820

<210> SEQ ID NO 5
<211> LENGTH: 11
<212> TYPE: PRT
<213> ORGANISM: Homo sapiens

<400> SEQUENCE: 5

His Thr Gln Glu Ala Gln Lys Glu Ala Gln Arg
1               5                   10

<210> SEQ ID NO 6
<211> LENGTH: 3582
<212> TYPE: DNA
<213> ORGANISM: Homo sapiens
<220> FEATURE:
<221> NAME/KEY: CDS
<222> LOCATION: (401)..(553)

<400> SEQUENCE: 6
acagaagaaa tagcaagtgc cgagaagctg catcagaaa aacagagggg agatttgtgt         60
ggctgcagcc gagggagacc aggaagatct gcatggtggg aaggacctga tgatacagag       120
```

```
gaattacaac acatatactt agtgtttcaa tgaacaccaa gataaataag tgaagagcta      180
gtccgctgtg agtctcctca gtgacacagg gctggatcac catcgacggc actttctgag      240
tactcagtgc agcaaagaaa gactacagac atctcaatgg caggggtgag aaataagaaa      300
ggctgctgac tttaccatct gaggccacac atctgctgaa atggagataa ttaacatcac      360
tagaaacagc aagatgacaa tataatgtct aagtagtgac atg ttt ttg cac att      415
                                              Met Phe Leu His Ile
                                              1               5 tcc agc ccc ttt aaa tat cca cac aca cag gaa gca caa aag gaa gca      463
Ser Ser Pro Phe Lys Tyr Pro His Thr Gln Glu Ala Gln Lys Glu Ala
        10                  15                  20 cag aga tcc ctg gga gaa atg ccc ggc cgc cat ctt ggg tca tcg atg      511
Gln Arg Ser Leu Gly Glu Met Pro Gly Arg His Leu Gly Ser Ser Met
            25                  30                  35 agc ctc gcc ctg tgc ctg gtc ccg ctt gtg agg gaa gga cat              553
Ser Leu Ala Leu Cys Leu Val Pro Leu Val Arg Glu Gly His
        40                  45                  50 tagaaaatga attgatgtgt ccttaaagg atgggcagga aaacagatcc tgttgtggat      613
atttatttga acgggattac agatttgaaa tgaagtcaca aagtgagcat taccaatgag      673
aggaaaacag acgagaaaat cttgatggct tcacaagaca tgcaacaaac aaaatggaat      733
actgtgatga catgaggcag ccaagctggg gaggagataa ccacggggca gagggtcagg      793
attctggccc tgctgcctaa actgtgcgtt cataaccaaa tcatttcata tttctaaccc      853
tcaaaacaaa gctgttgtaa tatctgatct ctacggttcc ttctgggccc aacattctcc      913
atatatccag ccacactcat ttttaatatt tagttcccag atctgtactg tgaccttcct      973
acactgtaga ataacattac tcattttgtt caaagaccct tcgtgttgct gcctaatatg     1033
tagctgactg ttttttcctaa ggagtgttct ggcccagggg atctgtgaac aggctgggaa    1093
gcatctcaag atctttccag ggttatactt actagcacac agcatgatca ttacggagtg    1153
aattatctaa tcaacatcat cctcagtgtc tttgcccata ctgaaattca tttcccactt    1213
ttgtgcccat tctcaagacc tcaaaatgtc attccattaa tatcacagga ttaactttt    1273 tttttaacct ggaagaattc aatgttacat gcagctatgg gaatttaatt acatattttg    1333
ttttccagtg caaagatgac taagtccttt atccctcccc tttgtttgat ttttttttcca    1393 gtataaagtt aaaatgctta gccttgtact gaggctgtat acagcacagc ctctccccat    1453
ccctccagcc ttatctgtca tcaccatcaa cccctcccat accacctaaa caaaatctaa    1513
cttgtaattc cttgaacatg tcaggacata cattattcct tctgcctgag aagctcttcc    1573
ttgtctctta aatctagaat gatgtaaagt tttgaataag ttgactatct tacttcatgc    1633
aaagaaggga cacatatgag attcatcatc acatgagaca gcaaatacta aaagtgtaat    1693
ttgattataa gagtttagat aaatatatga atgcaagag ccacagaggg aatgtttatg     1753
gggcacgttt gtaagcctgg gatgtgaagc aaaggcaggg aacctcatag tatcttatat    1813
aatatacttc atttctctat ctctatcaca atatccaaca agcttttcac agaattcatg    1873
cagtgcaaat ccccaaaggt aacctttatc catttcatgg tgagtgcgct ttagaatttt    1933
ggcaaatcat actggtcact tatctcaact ttgagatgtg tttgtccttg tagttaattg    1993
aaagaaatag ggcactcttg tgagccactt tagggttcac tcctggcaat aaagaattta    2053
caaagagcta ctcaggacca gttgttaaga gctctgtgtg tgtgtgtgtg tgtgtgtgag    2113
tgtacatgcc aaagtgtgcc tctctctctt gacccattat ttcagactta aaacaagcat    2173
gttttcaaat ggcactatga gctgccaatg atgtatcacc accatatctc attattctcc    2233
```

-continued

```
agtaaatgtg ataataatgt catctgttaa cataaaaaaa gtttgacttc acaaaagcag    2293
ctggaaatgg acaaccacaa tatgcataaa tctaactcct accatcagct acacactgct    2353
tgacatatat tgttagaagc acctcgcatt tgtgggttct cttaagcaaa atacttgcat    2413
taggtctcag ctggggctgt gcatcaggcg gtttgagaaa tattcaattc tcagcagaag    2473
ccagaatttg aattccctca tcttttagga atcatttacc aggtttggag aggattcaga    2533
cagctcaggt gctttcacta atgtctctga acttctgtcc ctctttgtgt tcatggatag    2593
tccaataaat aatgttatct ttgaactgat gctcatagga gagaatataa aactctgag    2653 tgatatcaac attagggatt caaagaaata ttagatttaa gctcacactg gtcaaaagga    2713
accaagatac aaagaactct gagctgtcat cgtccccatc tctgtgagcc acaaccaaca    2773
gcaggaccca acgcatgtct gagatcctta aatcaaggaa accagtgtca tgagttgaat    2833
tctcctatta tggatgctag cttctggcca tctctggctc tcctcttgac acatattagc    2893
ttctagcctt tgcttccacg acttttatct tttctccaac acatcgctta ccaatcctct    2953
ctctgctctg ttgctttgga cttccccaca agaatttcaa cgactctcaa gtcttttctt    3013
ccatccccac cactaacctg aattgcctag acccttattt ttattaattt ccaatagatg    3073
ctgcctatgg gctaatattg ctttagatga acattagata tttaaagtct aagaggttca    3133
aaatccaact cattatcttc tctttctttc acctcccctg ctcctctccc tatattactg    3193
attgactgaa caggatggtc cccaagatgc cagtcaaatg agaaacccag tggctccttg    3253
tggatcatgc atgcaagact gctgaagcca gaggatgact gattacgcct catgggtgga    3313
ggggaccact cctgggcctt cgtgattgtc aggagcaaga cctgagatgc tccctgcctt    3373
cagtgtcctc tgcatctccc ctttctaatg aagatccata gaatttgcta catttgagaa    3433
ttccaattag gaactcacat gttttatctg ccctatcaat tttttaaact tgctgaaaat    3493 taagttttt caaatctgt ccttgtaaat tactttttct tacagtgtct tggcatacta    3553
tatcaacttt gattctttgt tacaactttt                                     3582
```

<210> SEQ ID NO 7
<211> LENGTH: 51
<212> TYPE: PRT
<213> ORGANISM: Homo sapiens

<400> SEQUENCE: 7

Met Phe Leu His Ile Ser Ser Pro Phe Lys Tyr Pro His Thr Gln Glu
1               5                   10                  15

Ala Gln Lys Glu Ala Gln Arg Ser Leu Gly Glu Met Pro Gly Arg His
            20                  25                  30

Leu Gly Ser Ser Met Ser Leu Ala Leu Cys Leu Val Pro Leu Val Arg
        35                  40                  45

Glu Gly His
    50

<210> SEQ ID NO 8
<211> LENGTH: 74
<212> TYPE: DNA
<213> ORGANISM: Homo sapiens

<400> SEQUENCE: 8

```
ggatccacag aagaaatagc aagtgccgag aagctggcat cagaaaaaca gaggggagat    60
ttgtgtggct gcag                                                      74
```

<210> SEQ ID NO 9

```
<211> LENGTH: 123
<212> TYPE: DNA
<213> ORGANISM: Homo sapiens

<400> SEQUENCE: 9
gacagaagaa atagcaagtg ccgagaagct ggcatcagaa aaacagaggg gagatttgtg      60
tggctgcagc cgagggagac caggaagatc tgcatggtgg gaaggacctg atgatacaga    120
ggt                                                                   123
```